(12) United States Patent
Balbierz et al.

(10) Patent No.: US 10,568,675 B2
(45) Date of Patent: Feb. 25, 2020

(54) BONE TREATMENT SYSTEMS AND METHODS

(71) Applicant: DFINE, INC., South Jordan, UT (US)

(72) Inventors: Daniel J. Balbierz, Redwood City, CA (US); Eric K. Wong, Sunnyvale, CA (US)

(73) Assignee: DFine, Inc., South Jordan, UT (US)

( * ) Notice: Subject to any disclaimer, the term of this patent is extended or adjusted under 35 U.S.C. 154(b) by 440 days.

(21) Appl. No.: 15/313,080

(22) PCT Filed: Aug. 14, 2015

(86) PCT No.: PCT/US2015/045383
§ 371 (c)(1),
(2) Date: Nov. 21, 2016

(87) PCT Pub. No.: WO2016/028645
PCT Pub. Date: Feb. 25, 2016

(65) Prior Publication Data
US 2017/0209197 A1    Jul. 27, 2017

Related U.S. Application Data

(60) Provisional application No. 62/040,847, filed on Aug. 22, 2014.

(51) Int. Cl.
*A61B 17/88* (2006.01)
*A61B 17/00* (2006.01)

(52) U.S. Cl.
CPC ...... *A61B 17/8822* (2013.01); *A61B 17/8805* (2013.01); *A61B 17/8811* (2013.01); *A61B 17/8816* (2013.01); *A61B 17/8819* (2013.01); *A61B 2017/00539* (2013.01)

(58) Field of Classification Search
CPC .................................................. A61B 17/8822
See application file for complete search history.

(56) References Cited

U.S. PATENT DOCUMENTS

| 8,617,053 B2 | 12/2013 | Donovan et al. |
| 2005/0070915 A1 | 3/2005 | Mazzuca et al. |
| 2006/0074433 A1 | 4/2006 | McGill et al. |
| 2006/0116643 A1 | 6/2006 | Dixon et al. |
| 2006/0264967 A1 | 11/2006 | Ferreyro et al. |
| 2012/0191101 A1 | 7/2012 | Roth et al. |

FOREIGN PATENT DOCUMENTS

EP    2319440    5/2011

OTHER PUBLICATIONS

European Search Report dated Mar. 26, 2018 for EP15833393.0.

*Primary Examiner* — Andrew Yang
(74) *Attorney, Agent, or Firm* — Stoel Rives LLP

(57) ABSTRACT

A system for delivering bone cement into a bone is provided. The system can include a hydraulic system actuatable to deliver a bone cement mixture from a bone cement container, through a cannula and into a bone. The hydraulic system can have more than one pressure relief mechanism for decreasing pressure in the hydraulic system to cease delivery (e.g., substantially instantaneously) of the bone cement into the bone.

10 Claims, 16 Drawing Sheets

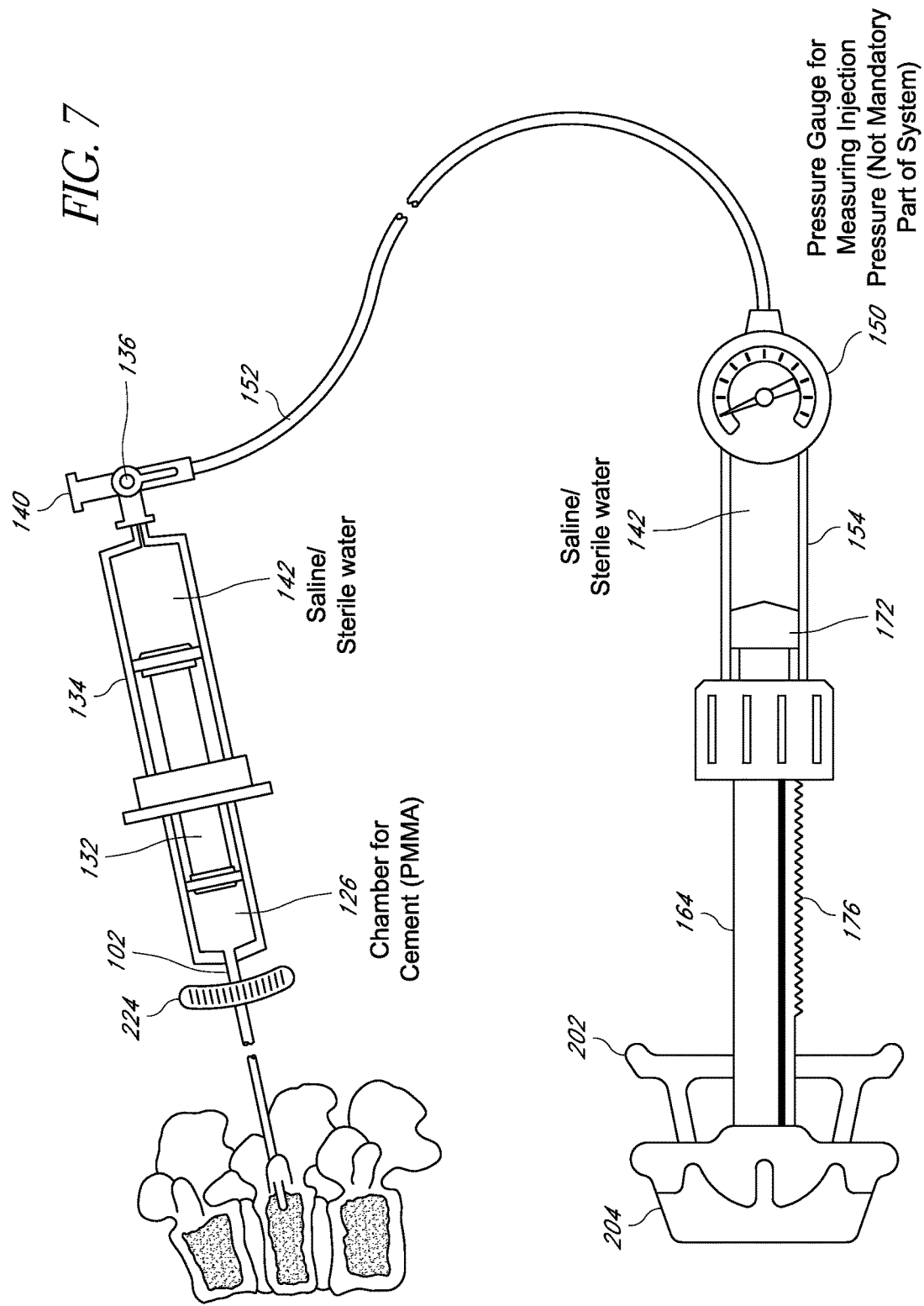

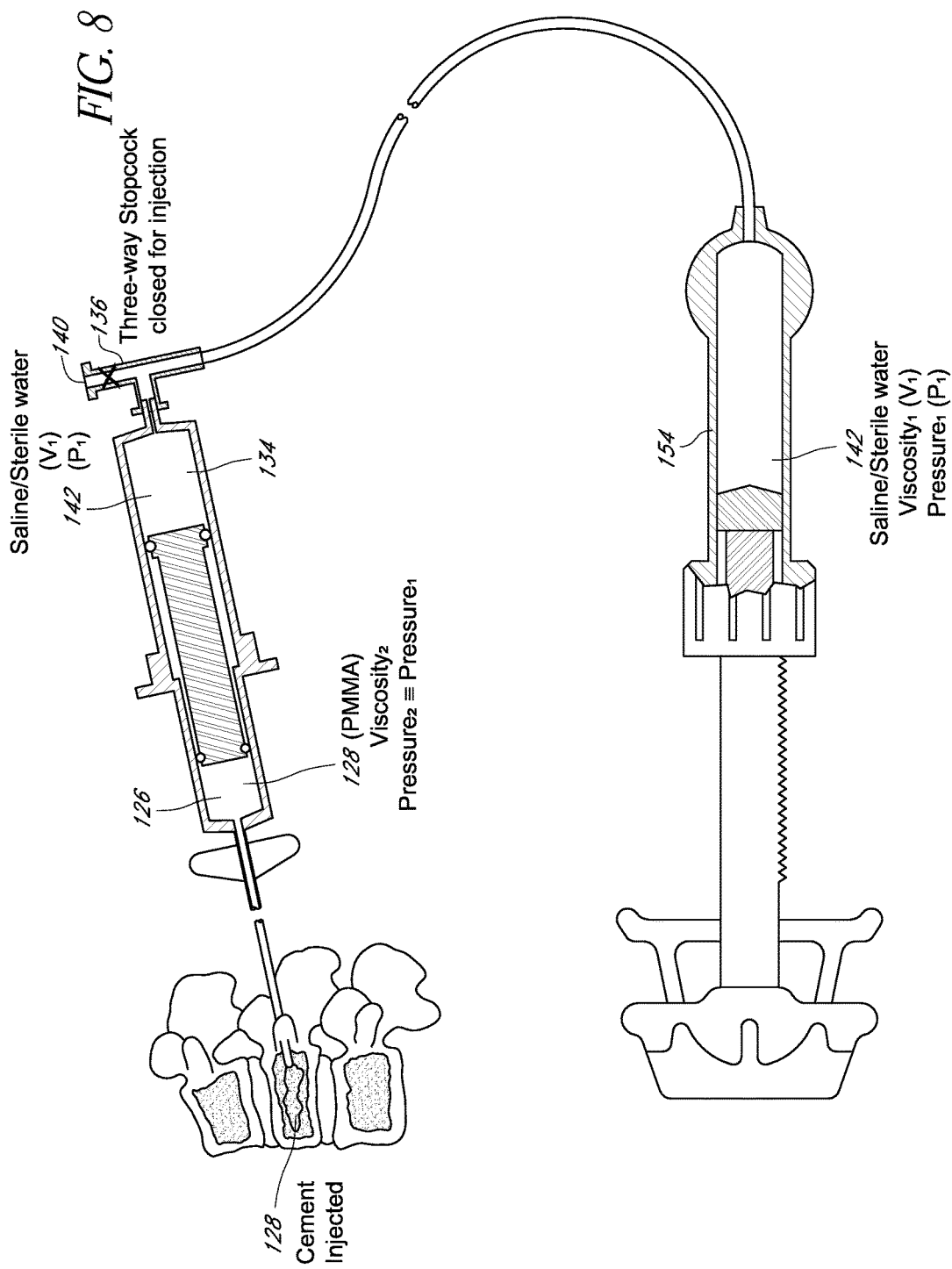

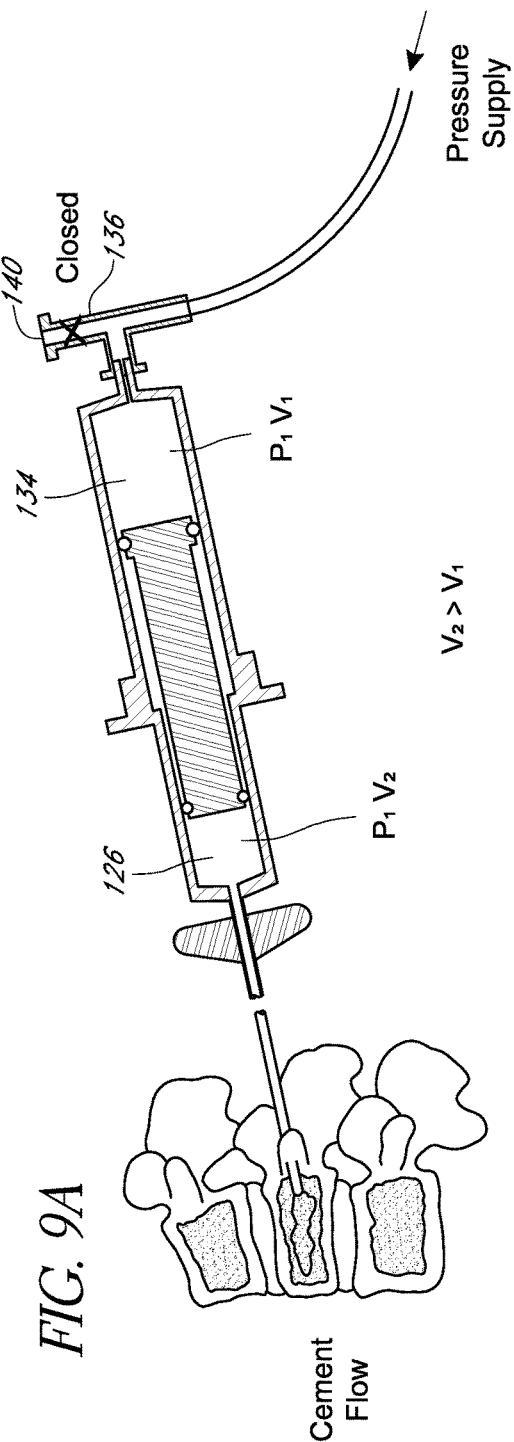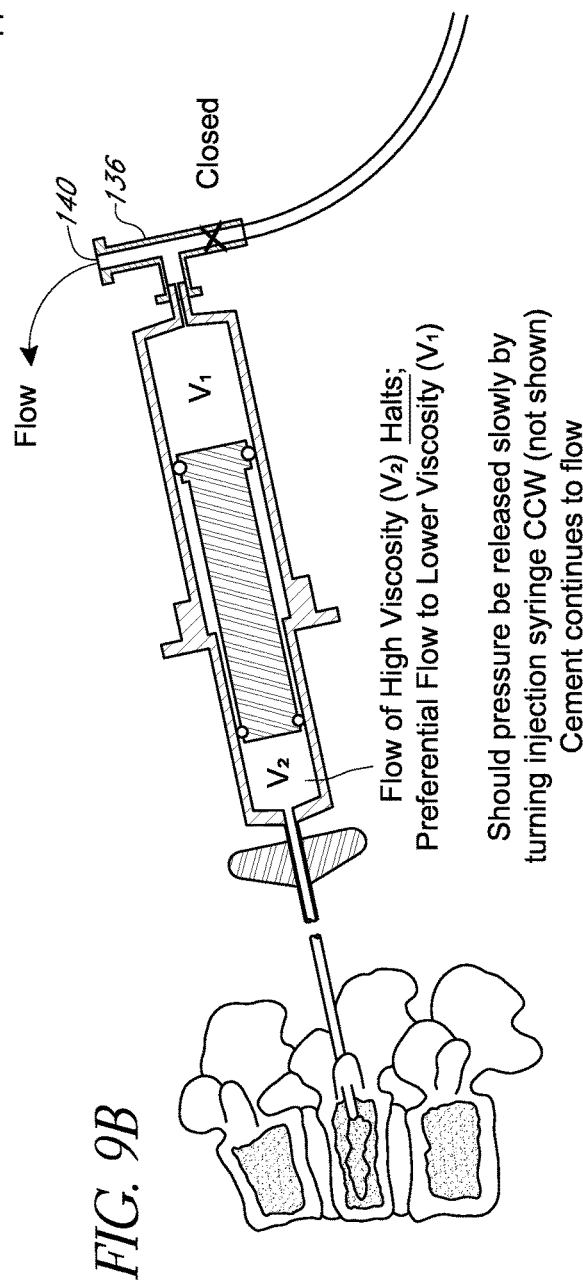
FIG. 9A
FIG. 9B

BONE TREATMENT SYSTEMS AND METHODS

BACKGROUND

Field

The present invention relates to bone cement injection systems and methods for osteoplasty procedures, such as vertebral compression fractures. In particular, one embodiment provides a system for delivery bone cement and a mechanism for controlling the flow of the bone cement. Another embodiment provides a method for using such system.

Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not proved solutions to this problem. Further, the population affected will grow steadily as life expectancy increases.

Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, made up of collagen, calcium salts and other minerals. Cancellous bone is similar to a honeycomb, with blood vessels and bone marrow in the spaces. Osteoporosis is a condition of decreased bone mass leading to fragile bones with an increased risk of fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to include osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be is forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See Groen, R. et al., "Anatomical and Pathological Considerations in Percutaneous Vertebroplasty and Kyphoplasty: A Reappraisal of the Vertebral Venous System", Spine, V. 29, No. 13, pp 1465-1471 (2004). Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures", J. Korean Neurosurg. Soc., V. 35, No. 5 (2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of an adjacent vertebral body. See Am. J. Neuroradiol., 25(2):175-80 (February 2004). This study found that 58% of vertebral bodies adjacent to a disc with cement leakage fractured during the follow-up period, compared with 12% of vertebral bodies adjacent to a disc without cement leakage.

Another life-threatening complication of vertebroplasty is pulmonary embolism. See Bernhard, J. et al., "Asymptomatic diffuse pulmonary embolism caused by acrylic cement: an unusual complication of percutaneous vertebroplasty", Ann. Rheum. Dis., 62:85-86 (2003). The vapors from PMMA preparation and injection also are cause for concern. See Kirby, B. et al., "Acute bronchospasm due to exposure to polymethylmethacrylate vapors during percutaneous vertebroplasty", Am. J. Roentgenol., 180:543-544 (2003).

In both higher pressure cement injection (vertebroplasty) and balloon-tamped cementing procedures (kyphoplasty), the methods involved do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, kyphoplasty balloons under very high pressure typically apply forces to vertebral endplates within a central region of the cortical bone that may be weak, rather than distributing forces over the endplate.

SUMMARY

There is a general need to provide bone cement delivery systems and methods for use in treatment of vertebral compression fractures that provide a greater degree of control over introduction of cement.

In accordance with one embodiment, a system for delivering bone cement into a bone is provided. The system can include a hydraulic system actuatable to deliver a bone cement mixture from a bone cement container, through a cannula and into a bone. The hydraulic system can have more than one pressure relief mechanism for decreasing pressure in the hydraulic system to cease delivery (e.g., substantially instantaneously) of the bone cement into the bone.

In accordance with one embodiment a system for delivering bone cement into a bone is provided. The system can include a bone cement injector extending along a longitudinal axis and having a channel extending therethrough to a distal opening. The bone cement injector can be at least partially percutaneously insertable into a bone. The system can include a bone cement delivery container removably coupled to a proximal end of the bone cement injector and in fluid communication with the channel. The system can include a distal hydraulic fluid container removably coupled to a proximal end of the bone cement delivery container. The system can include a slave piston having a proximal end disposed and slidably movable in the distal hydraulic fluid container and a distal end disposed and slidably movable in the bone cement delivery container. The distal end of the slave piston and a distal end of the bone cement delivery container can define a first chamber which can hold a bone cement mixture therein. The proximal end of the slave piston and proximal end of the distal hydraulic fluid container can define a second chamber which can hold a hydraulic fluid therein. The hydraulic fluid can have a lower viscosity than the bone cement mixture. The system can include a hydraulic line operably coupled to the proximal end of the distal hydraulic fluid container via a 3-way stopcock valve selectively acutatable to fluidly communicate the hydraulic line with the second chamber or isolate the hydraulic line from the second chamber. The system can include a proximal hydraulic fluid container removably coupled to and in fluid communication with a proximal end of the hydraulic line. The proximal hydraulic fluid container can define a third chamber which can hold the hydraulic fluid therein. The system can include an actuator movably coupled to the proximal hydraulic fluid container. The actuator can have a master piston and a control mechanism selectively actuatable to move the master piston incrementally within the third chamber or to slidably move the master piston within the third chamber. The system can be arranged such that actuation of the actuator to move the master piston distally in the third chamber causes hydraulic fluid to flow from the third chamber to the second chamber when the stopcock valve is positioned to fluidly communicate the hydraulic line with the second chamber, causing the slave piston to move distally to eject bone cement from the first chamber, through the bone cement injector and into the bone. The system can be arranged such that delivery of bone cement out of the bone cement injector is ceased substantially instantaneously via one or both of actuation of the stopcock valve to fluidly communicate the second chamber with a bypass chamber such that hydraulic fluid from the second chamber flows to the bypass chamber to cause the slave piston to move proximally and actuation of the actuator to slidably move the master piston proximally, thereby drawing hydraulic fluid from the second chamber into the third chamber to cause the slave piston to move proximally.

The system can be arranged such that the actuator comprises a shaft having a surface with a plurality of teeth along a length of the shaft, the teeth which can engage a threaded bore in a proximal portion of the proximal hydraulic fluid container, wherein the teeth are movable by the control mechanism between a first position where they engage the threaded bore to allow incremental movement of the master piston in the third chamber and a second position where they do not engage the threaded bore to allow non-incremental free sliding movement of the master piston in the third chamber. The system can be arranged such that in the first position the master piston is incrementally moved in the third chamber upon rotation of the control mechanism, and wherein in the second position the master piston is freely slid within the third chamber upon translation of the control mechanism. The control mechanism can include a ratchet and a pawl. The system can be arranged such that in the first position the pawl engages the ratchet to permit incremental changes in pressure upon translation of the control mechanism, and wherein in the second position the pawl disengages the ratchet to permit greater than the incremental changes in pressure upon translation of the control mechanism. The system can be arranged such that in the first position the pawl engages the ratchet to permit only incremental increases in pressure in the second chamber.

In accordance with one embodiment a system for delivering bone cement into a bone is provided. The system can include a bone cement injector extending along a longitudinal axis and having a channel extending therethrough to a distal opening. The bone cement injector can be at least partially percutaneously insertable into a bone. The system can include a bone cement delivery container removably coupled to a proximal end of the bone cement injector and in fluid communication with the channel. The system can include a master-slave hydraulic assembly removably coupled to a proximal end of the bone cement delivery container. A slave portion of the master-slave hydraulic assembly can include a slave piston having a distal end disposed and slidably movable in the bone cement delivery container and defining a first chamber which can hold a bone cement mixture therein between the distal end of the slave piston and a distal end of the bone cement delivery container. The system can include a control mechanism operably coupled to a master portion of the master-slave hydraulic assembly. The control mechanism can be actuatable to incrementally increase hydraulic pressure to cause the slave piston to move so as to controllably expel the bone cement mixture from the first chamber, through the injector and into bone. The control mechanism can be further selectively actuatable to increase or decrease hydraulic pressure non-incrementally. The system can be arranged such that delivery of bone cement out of the bone cement injector is ceased substantially instantaneously via one or both of actuation of a bypass valve in the master-slave hydraulic assembly that causes a decrease of pressure in the hydraulic assembly and causes the slave piston to move proximally and actuation of the control mechanism to decrease pressure in the hydraulic assembly in a non-incremental manner to cause the slave piston to move proximally.

The system can be arranged such that the control mechanism comprises a ratchet and a pawl. The system can be arranged such that in a first position the pawl engages the ratchet to permit incremental changes in pressure upon translation of the control mechanism, and wherein in a second position the pawl disengages the ratchet to permit greater than the incremental changes in pressure upon translation of the control mechanism. The system can be arranged such that in the first position the pawl engages the ratchet to permit only incremental increases in pressure in the second chamber.

In accordance with one embodiment a method for injecting bone cement into a bone is provided. The method can include the step of inserting at least a distal portion of a cannula percutaneously into a bone. The method can include the step of manually actuating a master-slave hydraulic assembly to deliver a bone cement mixture from a bone cement container through the cannula and into the bone. The method can include the step of manually actuating a pressure release mechanism of the hydraulic assembly to reduce pressure in the master-slave hydraulic assembly to cease delivery of bone cement from the cannula substantially instantaneously.

The step of actuating the pressure release mechanism comprises actuating one or both of a) a bypass valve that causes a decrease of pressure in the hydraulic assembly and causes a slave piston to move proximally within the bone cement container and b) actuating an actuator operably coupled to the master-slave hydraulic assembly to decrease pressure in the hydraulic assembly in a non-incremental manner to cause the slave piston to move proximally.

BRIEF DESCRIPTION OF THE DRAWINGS

FIG. 7 is a schematic view of the of the injection system of FIG. 2.

FIG. 8 is a schematic view of the of the injection system of FIG. 2 showing the relative pressures and viscosities.

FIG. 9A is a schematic view of the of the injection system of FIG. 2 with the stopcock closed.

FIG. 9B is a schematic view of the of the injection system of FIG. 2 with the stopcock open.

DETAILED DESCRIPTION

Figure 1A:
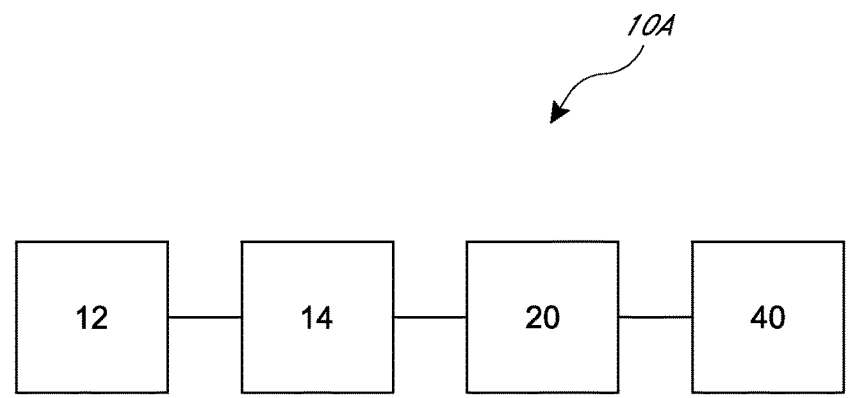
FIG. 1A is a block diagram of an embodiment of an injection system for delivering bone cement into a bone.

For purposes of understanding the principles of the invention, reference will now be made to the embodiments illustrated in the drawings and the accompanying text. As background, a vertebroplasty procedure could include inserting an injector of the system of FIGS. 1-14 through a pedicle of a vertebra, or via a parapedicular approach, for accessing the osteoporotic cancellous bone. The initial aspects of the procedure can be similar to a conventional percutaneous vertebroplasty wherein the patient can be placed in a prone position on an operating table. The patient is typically under conscious sedation, although general anesthesia is an alternative. The physician can inject a local anesthetic (e.g., 1% Lidocaine) into the region overlying the targeted pedicle or pedicles as well as the periosteum of the pedicle(s). Thereafter, the physician can use a scalpel to make a 1 to 5 mm skin incision over each targeted pedicle. Thereafter, the introducer is advanced through the pedicle into the anterior region of the vertebral body, which typically is the region of greatest compression and fracture. The physician can confirm the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

Definitions

"Bone cement, bone fill or fill material, infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Fluid" is used in its broadest sense, to refer to any fluid, including both liquids and gasses as well as solutions, compounds, suspensions, etc., which generally behave as a fluid.

"Substantially" or "substantial" mean largely but not entirely. For example, substantially may mean about 50% to about 99.999%, about 80% to about 99.999% or about 90% to about 99.999%.

"Vertebroplasty" includes its ordinary meaning and means any procedure wherein fill material is delivered into the interior of a vertebra.

"Osteoplasty" includes its ordinary meaning and means any procedure wherein fill material is delivered into the interior of a bone.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

The present disclosure advantageously provides a system for delivering bone cement into a bone. The system can include a hydraulic system actuatable to deliver a bone cement mixture from a bone cement container, through a cannula and into a bone. The hydraulic system can have more than one pressure relief mechanism for decreasing pressure in the hydraulic system to cease delivery (e.g., substantially instantaneously) of the bone cement into the bone.

FIG. 1A schematically shows a bone cement delivery system 10A that includes a bone cement injector (e.g., cannula) 12 that can extend at least partially into a bone (e.g., a vertebral body). The bone cement injector 12 can be made of any suitable metal or plastic needle-like member. The bone cement injector 12 can include a proximal end, a distal end, and a flow channel extending therethrough. The bone cement injector 12 can have a flow outlet near the distal end of the bone cement injector. The proximal end of the bone cement injector 12 can include a fitting for coupling a bone cement container 14 thereto.

The bone cement container 14 can be detachable and coupleable to the fitting, and thereby in fluid communication with the flow channel in the bone cement injector 12. The bone cement container 14 can receive and hold a bone cement mixture therein, which can be delivered through an outlet of the container 14, through the flow channel in the injector 12 and into the bone. A hydraulic assembly 20 can be operably coupled to the container 14 and operated to impart a force onto the bone cement mixture to expel the bone cement mixture from the container 14, through the injector 12 and into the bone. The hydraulic assembly 20 can hold a hydraulic fluid (e.g., saline, water) that has a lower viscosity than the bone cement mixture. Optionally, the hydraulic assembly can be a closed hydraulic system. The bone cement delivery system 10A also includes a control mechanism 40 operably coupled to the hydraulic assembly and acutatable by a user to actuate the hydraulic assembly to impart said force. The system 10A can have one or more pressure relief mechanisms for decreasing pressure in the hydraulic assembly to cease delivery (e.g., substantially instantaneously, such as within less than 2 seconds, less than 1 second, less than 0.5 seconds, less than 0.3 seconds, less than 0.1 seconds, etc.) of the bone cement into the bone, for example, by removing hydraulic fluid from the hydraulic assembly (e.g., venting to the atmosphere, expelling to a bypass chamber).

Figure 1B:
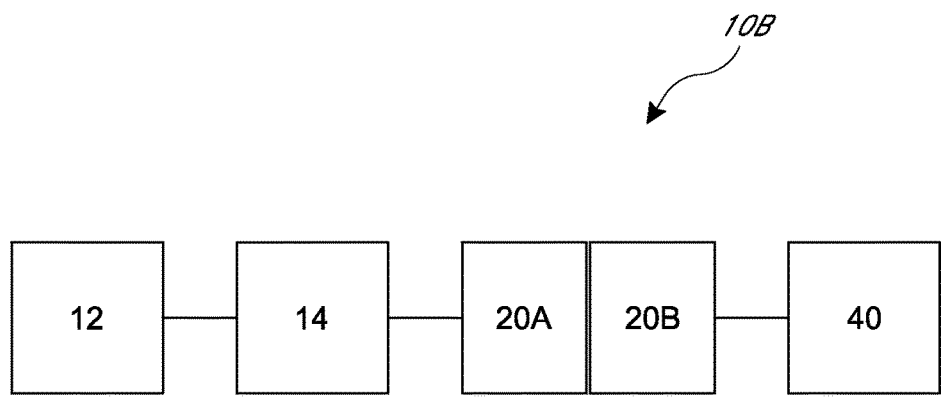
FIG. 1B is a block diagram of an embodiment of an injection system for delivering bone cement into a bone.

FIG. 1B schematically shows another embodiment of an injection system 10B for delivering bone cement into a bone. The injection system 10B is identical to the system 10A shown in FIG. 1A except as described below. Thus, the reference numerals used to designate the various components of the system 10B are identical to those used for identifying the corresponding components of the system 10A in FIG. 1A, except as noted below. In the illustrated embodiment, the hydraulic assembly 20 can include a distal hydraulic chamber 20A and a proximal hydraulic chamber 20B, wherein hydraulic pressure generated in the proximal hydraulic chamber 20B by the control mechanism 40 is communicated to the distal hydraulic chamber 20A, which then operates an actuator to impart a force (e.g., with mechanical advantage) on the bone cement mixture in the container 14. Optionally, the proximal and distal hydraulic chambers 20B, 20A can be separate hydraulic containers that are directly coupled to each other. Alternatively, the proximal and distal hydraulic chambers 20B, 20A can be part of a single monolithic hydraulic container.

Figure 1C:
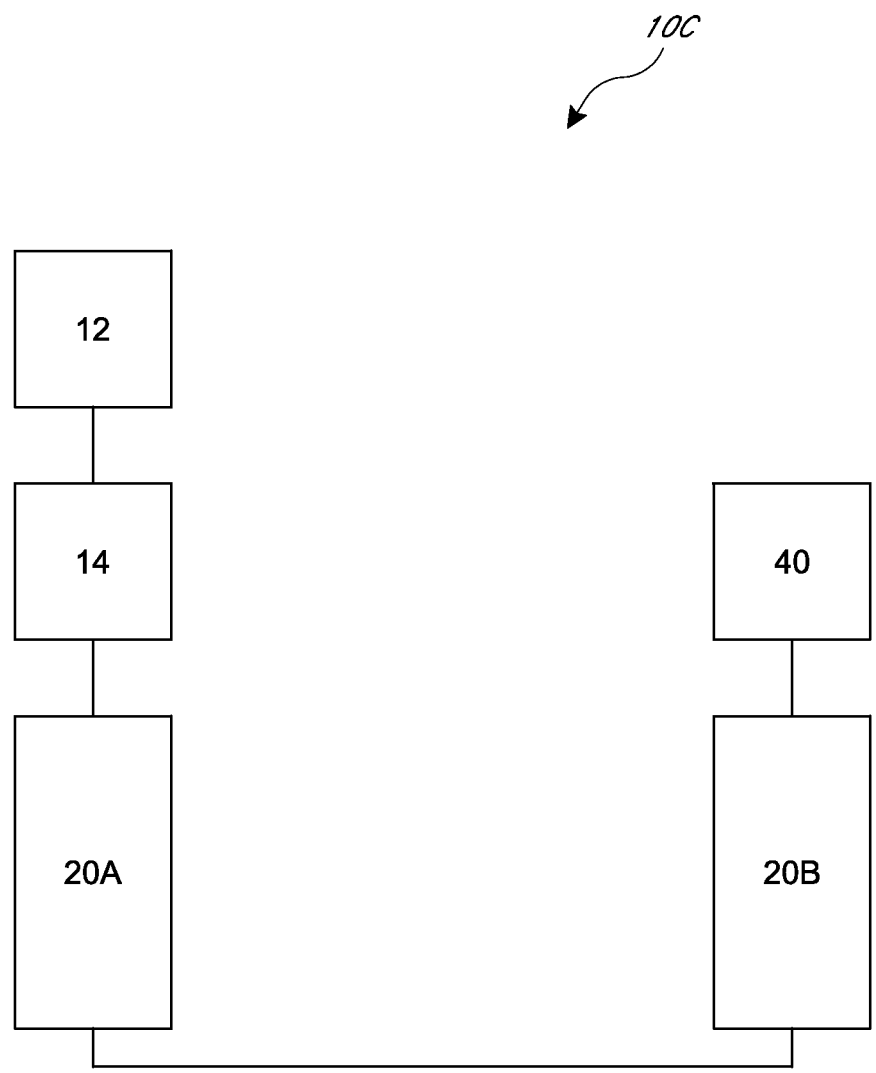
FIG. 1C is a block diagram of an embodiment of an injection system for delivering bone cement into a bone.

FIG. 1C schematically shows another embodiment of an injection system 10C for delivering bone cement into a bone. The injection system 10C is identical to the system 10B shown in FIG. 1B except as described below. Thus, the reference numerals used to designate the various components of the system 10C are identical to those used for identifying the corresponding components of the system 10B in FIG. 1B, except as noted below. In the illustrated embodiment, the distal hydraulic chamber 20A and proximal hydraulic chamber 20B are fluidly connected via a hydraulic line 30, so that hydraulic pressure generated in the proximal hydraulic chamber 20B by the control mechanism 40 is communicated to the distal hydraulic chamber 20A via the line 30. Accordingly, the control mechanism 40 can advantageously be actuated by the user from a remote location relative to the patient (e.g., to reduce exposure to radiation, provide a more open or less cluttered surgical filed where space is limited, etc.).

Now turning to FIGS. 2-6, one embodiment of the bone cement delivery system 100 is shown. The bone cement delivery system 100 includes a bone cement injector 102 that can extend at least partially into a vertebra. The bone cement injector 102 can be a cannula, which in some embodiments is long and thin. The bone cement injector 102 can be formed of any suitable material, including metal and plastic. The bone cement injector 102 includes a proximal end 104 and a distal end 106 and a flow channel (not shown) extending therethrough. The flow channel extends about the axis 108. The distal end 106 includes a flow outlet 112. In some embodiments, the flow outlet 112 is aligned with the axis 108, and in other embodiments, the flow outlet 112 is offset from the axis 108 (e.g., perpendicular to the axis 108).

The proximal end 104 of bone cement injector 102 has a fitting 114. In some embodiments, the fitting 114 is a threaded post having a channel therein. The fitting 114 engages a complementary fitting 118 of a bone cement chamber 116. In some embodiments, the fitting 114 is a threaded post and the complementary fitting 118 is a threaded bore. In some embodiments, the bone cement injector 102 can include a bar 122. The bar 122 can be firmly coupled and/or integrally formed with the fitting 114. The bar 122 can be coupled with a trocar, shown in FIGS. 15-16 for the initial introduction of the injector 102 to the vertebral body site, after which the trocar handle can be decoupled from the bar 122 and the trocar removed from the channel of the injector 102, leaving the injector 102 in place. The bone cement injector 102 can include a knob 120. The knob 120 can facilitate the rotation and translation of the bone cement injector 102 and/or the trocar, as described herein.

The bone cement chamber 116 is shown with a syringe body 124 with cement-carrying chamber 126. The cement-carrying chamber 126 can carry, in one embodiment, a pre-polymerized, partially polymerized or recently-mixed bone cement 128 therein. The bone cement chamber 126 is further shown with an actuator member 132. In some embodiments, the actuator member 132 is a floating piston. The actuator member 132 includes o-ring or rubber head or interface 148 that can slidably move in the chamber 126. Upon actuation, the actuator member 132 slides within the chamber 126 to push the bone cement 128 through the bone cement injector 102. In one embodiment, the bone cement (e.g., a polymer powder and a monomer liquid) is mixed within the syringe body 124, as described in U.S. Pat. No. 8,777,479, and the syringe body 124 thereafter coupled to the injector 102 and a floating piston at least partially introduced into the syringe body 124.

The system 100 has a distal hydraulic fluid container 134 that can be a cylinder that couples to a proximal end of the syringe body 124. The distal hydraulic fluid container 134 has a pressurizable chamber 138 therein that can slidably receive a proximal end of the actuator member 132. The chamber 138 can be pressurized with hydraulic fluid or flow media 142 to drive actuator member 132 distally toward the bone cement injector 102 to thereby displace bone cement 128 from chamber 126 to the bone cement injector 102. The flow media 142 is a less viscous material than the bone cement 128. In one embodiment, the flow media 142 is saline. In another embodiment, the flow media 142 is water. In one embodiment, the surface area of an interface 146 between the actuator member 132 and the pressurized flow media 142 can be substantially larger than the surface area of interface 148 between the actuator member 132 and the bone cement 128. The difference in surface area between the two interfaces 146, 148 can provide pressure amplification between the pressurizable chamber 138 and the chamber 126. In one embodiment, the surface area of interface 146 can be at least 150% of the surface area of interface 148, at least 200% of the surface area of interface 148, at least 250% of the surface area of interface 148 and/or at least 300% of the surface area of interface 148.

In one embodiment, a force amplification method of the invention can include one or more of the following steps (a) providing a bone cement injector with a displaceable actuator component intermediate a first fluid chamber and a second bone cement carrying chamber; (b) causing a flow of flow media at a first pressure into the first fluid chamber thereby displacing the actuator component to impinge on and eject bone cement at a higher second pressure from the second chamber. The method can provide a second pressure in the cement-carrying chamber 126 that is: at least 25% higher than the first pressure in the pressurizable chamber 138, at least 50% higher than the first pressure in the pressurizable chamber 138, at least 100% higher than the first pressure in the pressurizable chamber 138, at least 200% higher than the first pressure in the pressurizable chamber 138, at least 300% higher than the first pressure in the pressurizable chamber 138.

The bone cement delivery system 100 can include a line 152 that extends between the distal hydraulic fluid container 134 and a proximal hydraulic fluid container 154. The line 152 can be connected to a three way stopcock 136. The stopcock 136 acts as a valve to restrict the flow of the flow media 142 through line 152. In some embodiments, the stopcock 136 is actuated to a first position or opened (or at 0 degrees) to allow the flow media 142 to travel between the distal hydraulic fluid container 134 and the proximal hydraulic fluid container 154. The stopcock 136 is actuated to a second position or closed (or at 90 degrees) to prevent the flow media 142 to travel between the distal hydraulic fluid container 134 and the proximal hydraulic fluid container 154. In some embodiments, the stopcock 136 is actuated to a third position (or at 180 degrees) to allow the hydraulic fluid flow media 142 to travel (from the proximal and distal hydraulic fluid containers 154, 134) through an opening 140 to a bypass container (not shown) or vented to the atmosphere.

The stopcock 136 can be located at any position along the line 152. In the illustrated embodiment, the stopcock 136 is located near the distal hydraulic fluid container 134. The stopcock 136 can be coupled to the proximal end of the distal hydraulic fluid container 134, at one end of the line 152. This location could be closer for a surgical assistant or other third person to reach and manipulate the stopcock 136. In other embodiments, the stopcock 136 is located near the proximal hydraulic fluid container 154. The stopcock 136 can be coupled to the end of the proximal hydraulic fluid container 154, at one end of the line 152. This location could be closer to reach and manipulate the stopcock 136 for a surgeon or user manipulating the control mechanism 162 described herein. Other configurations are contemplated (e.g., the stopcock 136 can be located in the line 152 at an intermediate position between the proximal hydraulic fluid container 154 and the distal hydraulic fluid container 134).

The bone cement delivery system 100 can optionally include a pressure gauge 150. The pressure gauge 150 can be located at any position along the line 152. In the illustrated embodiment, the pressure gauge 150 is located near the proximal hydraulic fluid container 154. The pressure gauge 150 can be coupled to the end of the proximal hydraulic fluid container 154, at one end of the line 152. This location could be closer to read the pressure gauge 150 for a surgeon or user manipulating the control mechanism 162 described herein. In other embodiments, the pressure gauge 150 is located near the distal hydraulic fluid container 134. Other configurations are contemplated. More than one pressure gauge 150 can be included.

FIGS. 2-10 illustrate one embodiment of the control mechanism 162. The control mechanism 162 has a first position and a second position. In both the first position and the second position, the stopcock 136 is closed to allow the flow media 142 to travel between the distal hydraulic fluid container 134 and the proximal hydraulic fluid container 154. The first position is associated with incremental movement of the pressurized flow media 142. The first position allows incremental increases or decreases in pressure between the proximal hydraulic fluid container 154 and the distal hydraulic fluid container 134. The first position allows for incremental movement of the control mechanism 162, resulting in incremental movement of flow media 142 between the proximal hydraulic fluid container 154 and the distal hydraulic fluid container 134, and thereby resulting in incremental movement of the actuator member 132. The control mechanism 162 can have a mating structure and a complementary mating structure that permits only incremental movement. The second position allows rapid increases or decreases in pressure between the proximal hydraulic fluid container 154 and the distal hydraulic fluid container 134. The mating structure and a complementary mating structure can disengage to allow for greater than incremental movement in said second position.

The second position of the control mechanism 162 can stop or prevent the flow of bone cement from the bone cement injector 102. For instance, the bone cement may continue to flow through the bone cement container 126 to the flow channel in the bone cement injector 102 in the absence of the transfer of fluids between the distal hydraulic fluid container 134 and the proximal hydraulic fluid container 154. The second position of the control mechanism 20 allows the rapid withdrawal (e.g., within less than 2 seconds, less than 1 second, less than 0.5 seconds, less than 0.3 seconds, less than 0.1 seconds) of fluid from the distal hydraulic fluid container 134 to the proximal hydraulic fluid container 154. This decrease in pressure in the distal hydraulic fluid container 134 can cause movement of the actuator member 132 in the chamber 126 away from the injector 102. The movement of the actuator member 132 can cause the bone cement 128 to retract into the chamber 126 thereby ceasing or preventing the flow of bone cement 128 through the bone cement injector 102 and into the bone.

The control mechanism 162 can be any suitable type of mechanism or pump that can actuate the actuator member 132 to move the bone cement 128 in the chamber 126. For example, a suitable mechanism can be a piezoelectric element for pumping fluid, an ultrasonic pump element, a compressed air system for creating pressure, a compressed gas cartridge for creating pressure, an electromagnetic pump for creating pressure, an air-hammer system for creating pressure, a mechanism for capturing forces from a phase change in a fluid media, a spring mechanism for releaseably storing energy, a spring mechanism and a ratchet, a fluid flow system and a valve, a screw pump, a peristaltic pump, a diaphragm pump, a rotodynamic pump or a positive displacement pump.

Figure 2:
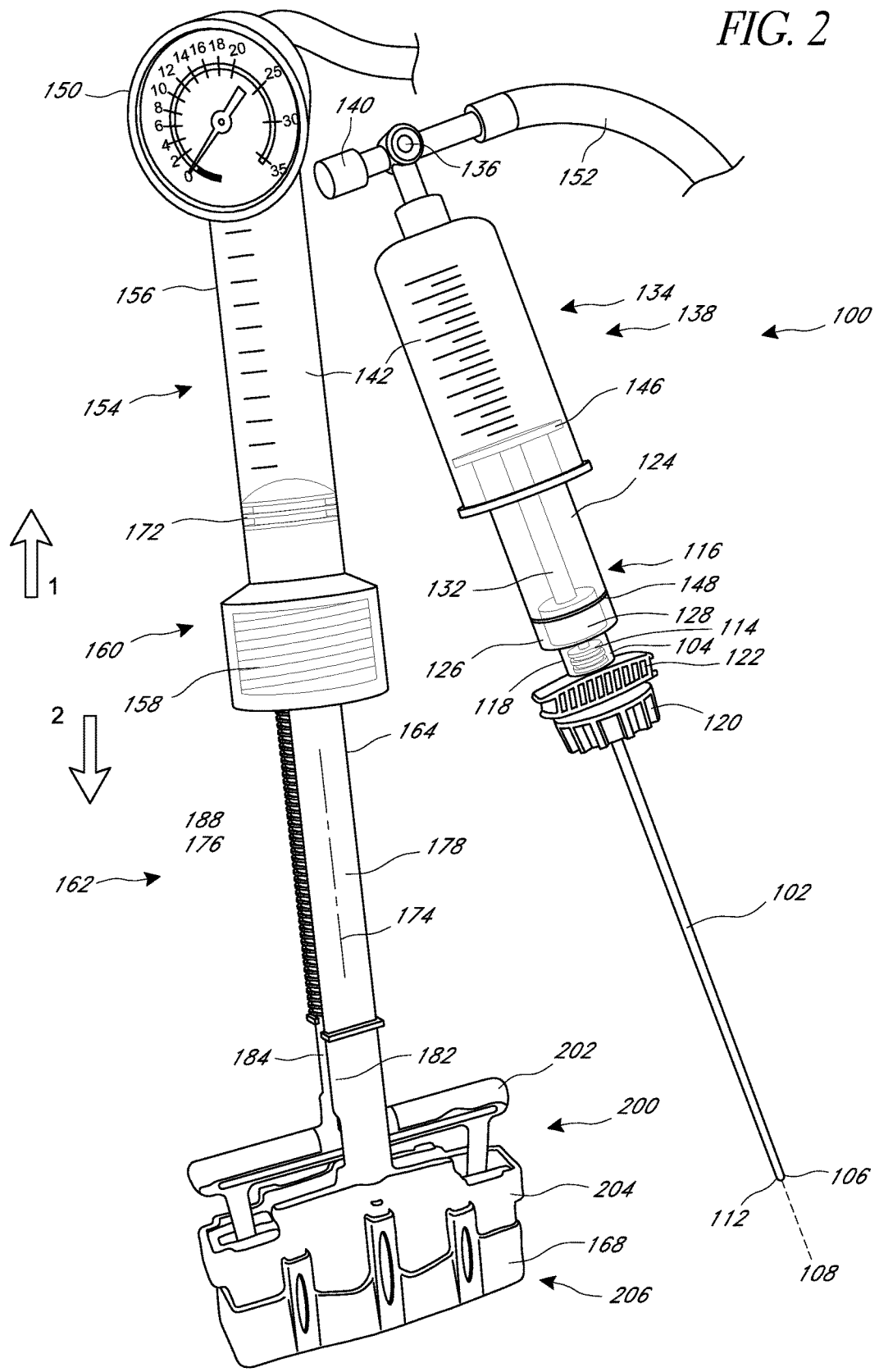
FIG. 2 is a perspective view of one embodiment of an injection system for delivering bone cement into a bone.

FIG. 2 shows the control mechanism 162 can comprise the elongate member 164 having a proximal end 168 and a distal end 172. The distal end 172 of the elongate member 164 may be longitudinally displaceable within the syringe body 156. The distal end 172 includes o-ring or rubber head that can slidably move in the syringe body 156. The elongate member 164 can include an axis 174 extending between the distal end 172 and the proximal end 168. The elongate member 164 can include a mating structure 176, described in greater detail herein.

The syringe body 156 of the proximal hydraulic fluid container 154 may be formed of a generally cylindrical hollow tube sized to receive an elongate member 164. The syringe body 156 may include an inlet/outlet port coupled to the line 152 located adjacent one end of the syringe body 156. In some embodiments, a nut 160 may be coupled to the syringe body 156 adjacent the other end of the syringe body 156. The nut 160 may include a center hole sized to allow the elongate member 164 to pass through the nut 160 into the syringe body 156. Further, the nut 160 may include a complementary mating structure 158 that selectively couples the nut 160 to a portion of the elongate member 164, described in greater detail herein.

A fluid reservoir of the proximal hydraulic fluid container 154 may be defined by the space enclosed by the inside walls of the syringe body 156 between the distal end 172 of the elongate member 164 and the end of the syringe body 156 near the line 152. Accordingly, movement of the distal end 172 of the elongate member 164 with respect to the syringe body 156 will alter the size and volume of the fluid reservoir of the proximal hydraulic fluid container 154.

The elongate member 164 may include a mating structure 176 that selectively couples the elongate member 164 to the nut 160. In the illustrated embodiment, the elongate member 164 may thus be translated longitudinally with respect to the syringe body 156 by rotating the elongate member 164 such that the interaction of the mating structure 176 and the complementary mating structure 158 results in the longitudinal translation of the elongate member 164. Thus, when the mating structure 176 and the complementary mating structure 158 are engaged, movement of the elongate member 164 is constrained with respect to the syringe body 156, though the elongate member 164 is not necessarily fixed with respect to the syringe body 156. For example, the elongate member 164 may be rotatable, but not directly translatable, when the mating structure 176 and the complementary mating structure 158 are engaged.

In the illustrated embodiment, the elongate member 164 includes an inner core 184 and an outer sheath 178. The outer sheath 178 can span the distance between the proximal end 168 and the distal end 172. The outer sheath 178 may be coupled to a handle 200 at the proximal end of the outer sheath 178 and the rubber head at the distal end of the outer sheath 178. The inner core 184 includes the mating structure 176. The inner core 184 is disposed within the outer sheath 178. The inner core 184 can be sized to permit movement within the outer sheath 178. In some embodiments, the advancement or retraction of the inner core 184 within the outer sheath 178 can cause the control mechanism 162 to change from a first position to a second position.

The outer sheath 178 may also include a cut out 182 sized to allow the mating structure 176 extend through. The interaction between these cut outs 182 and mating structure 176 constrains the movement of the inner core 184 with respect to the outer sheath 178; that is, the two components may only travel (with respect to each other) in a single direction, parallel to the longitudinal axis 174 of the elongate member 164. The mating structure 176 may be retracted into the cut out 182 and into the outer sheath 178. In some embodiments, the mating structure 176 and the cut out 182 extend less than 360 degrees around the axis of the elongate member 164.

In other embodiments, the outer sheath 178 comprises one or more cut outs 182 (two cut outs, three cut outs, four cut outs, etc.). The two or more cut outs 182 can be equally spaced around the circumference of the outer sheath 178. The one or more cut outs 182 can extend over a portion of the outer sheath 178, such as a portion near the distal end of the outer sheath 178. The one or more cut outs 182 can be longitudinally extending, parallel to the axis 174. Other designs of the outer sheath 178 are contemplated.

The angled surfaces 180 on the inner core 184 and the angled surfaces 190 within the outer sheath 178 interact such that the mating structure 176 may be retractable within the outer sheath 178. Translation of the inner core 184 in the proximal direction simultaneously causes the inner core 184 to retract toward the center axis of the outer sheath 178 due to the interaction of the angled surfaces 180 on the inner core 184 with the angled surfaces 190 within the outer sheath 178. Similarly, translation of the inner core 184 in the distal direction causes the inner core 184 to move away from the center axis of the outer sheath 178. In the illustrated embodiment, a distally oriented biasing force acting on the inner core 184 may bias the mating structure 176 to the second position. It will be appreciated by one of ordinary skill in the art having the benefit of this disclosure that it is within the scope of this disclosure to modify the angles and interfaces such that a distally oriented biasing force on the inner core 184 would bias the mating structure 176 in the first position.

The handle 200 broadly refers to the group of components coupled to the proximal end of the elongate member 164, some of which may be grasped by a user. In certain embodiments, the handle 200 can allow the user to manipulate the position of the elongate member 164 by manipulating the handle 200. Further, in some embodiments the handle 200 may be an actuator mechanism that can manipulate components of the control mechanism 162. The handle 200 broadly refers to the components coupled to the proximal end of the elongate member 164 which can be grasped by a user.

In the illustrated embodiment, the inner core handle 202 travels in a direction transverse to the longitudinal axis 174 of the elongate member 164 (in addition to travel along the longitudinal axis) when it is compressed, due to the interaction of the angled surfaces of the inner core 184 and the outer sheath 178. Ridges and slots, such as those of the illustrated embodiment, may provide a degree of usability and comfort to the handle 200. The outer sheath handle 204 can include a grip 206 that can be held by the surgeon. In the illustrated embodiment, the grip 206 extends generally perpendicular to the axis 174.

Embodiments which utilize the mating structure 176 and the complementary mating structure 158 may allow a user to displace the elongate member 164 relative to the syringe body 156 either through rotation of the elongate member 164 (and the subsequent interaction of threads), or by retracting the inner core 184 and displacing the elongate member 164 by applying opposing forces on the elongate member 164 and the syringe body 154. The forces, of course, may move the elongate member 164 distally or proximally with respect to the syringe body 156. Both methods of displacement may be utilized during the course of a single therapy.

In the illustrated embodiment of FIGS. 2-6, the mating structure 176 of the inner core 184 is a series of wedges 188. The wedges 188 can be equally shaped. The wedges 188 can extend along a portion of the inner core 184, such as a distal portion of the inner core 184. The wedges 188 can extend along a length of the inner core equal to the length of the syringe body 156. The wedges 188 can have a width less than or equal to the width of the cut out 182. The wedges 188 can be sized to extend from the cut out 182 of the outer sheath 178. The wedges 188 can have a substantially ramped surface 192 and a substantially flat surface 194. The substantially flat surface 194 of the wedges 188 may prevent the disengagement between the wedges 188 and the complementary mating structure 158.

In the illustrated embodiment, the complementary mating structure 158 of the proximal hydraulic fluid container 154 is a threaded bore 196. The wedges 188 and the outer sheath 178 can have a similar diameter as the threaded bore 196. In some embodiments, the wedges 188 are flexible to account for any misalignment between the wedges 188 and the threaded bore 196. The threaded bore 196 can be sized to permit a plurality of the wedges 188 (e.g., 6 wedges, 8 wedges, 10 wedges, 12 wedges, 14 wedges, etc.) to engage the threaded bore 196. The wedges 188 have a circumference smaller than the elongate member 164. The substantially flat surface 194 of the wedges 188 may prevent the disengagement between the wedges 188 and the threaded bore 196.

The substantially ramped surface 192 may allow the wedge 188 to function as a thread. For instance, the wedges 188 can have a pitch similar to the threaded bore 196. The thread like structure of the wedges 188 allows rotation motion to be translated to linear motion. The thread like structure of the wedges 188 also permits incremental changes in fluid displacement. For instance, a full rotation of the elongate member 164 may only displace a small volume of bone cement (e.g., about 0.5 mL, about 1 mL, about 1.5 mL, about 2 mL). Further, the thread like structure of the wedges 188 may prevent the disengagement between the elongate member 164 and the proximal hydraulic fluid container 154.

In some embodiments, the mating structure 176 of the inner core 184 has two sets of wedges. The first set of wedges can be substantially similar to the wedges 188 shown in FIGS. 2-6. The second set of wedges can be disposed at another circumferential location, such as offset by 180 degrees (not shown). The second set of wedges can provide a second point of contact between the mating structure 176 of the inner core 184 and the complementary mating structure 158 of the proximal hydraulic fluid container 154. In some embodiments, the two sets of wedges can be simultaneously retracted into the outer sheath 178 in the second position. In some embodiments, each set of wedges is independently retracted into the outer sheath 178 in the second position.

Figure 3:
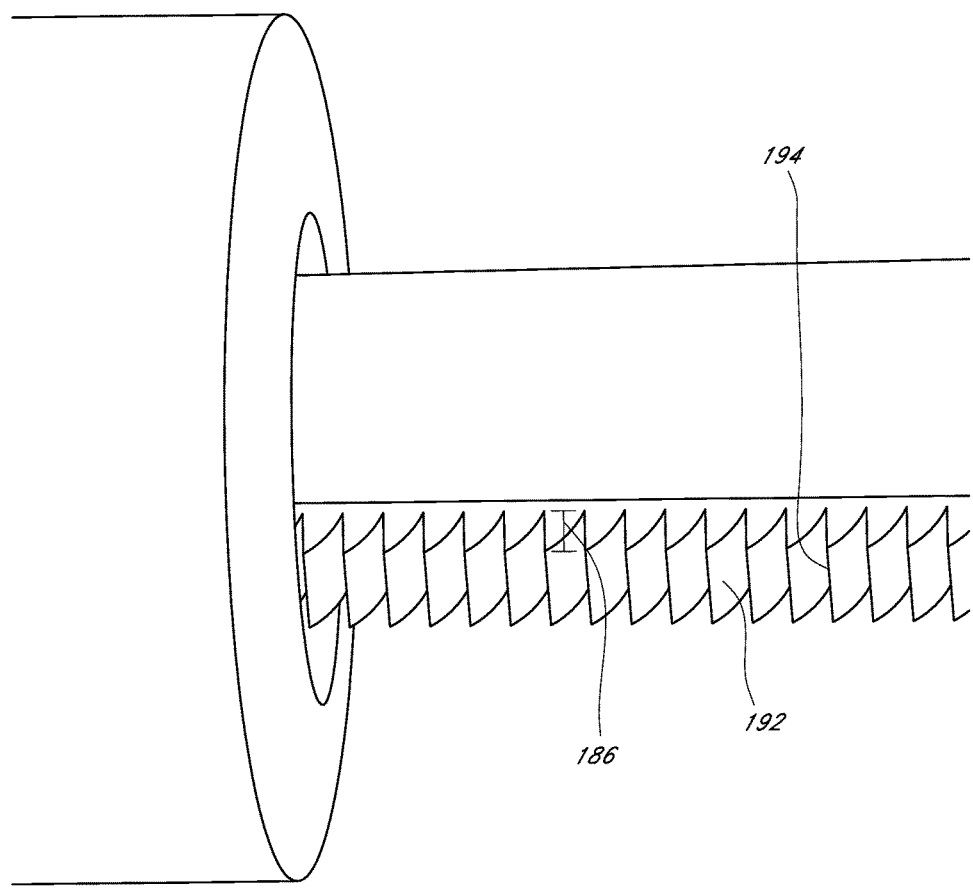
FIG. 3 is a perspective view of one embodiment of a control mechanism of the injection system of FIG. 2 in a first position.
Figure 4:
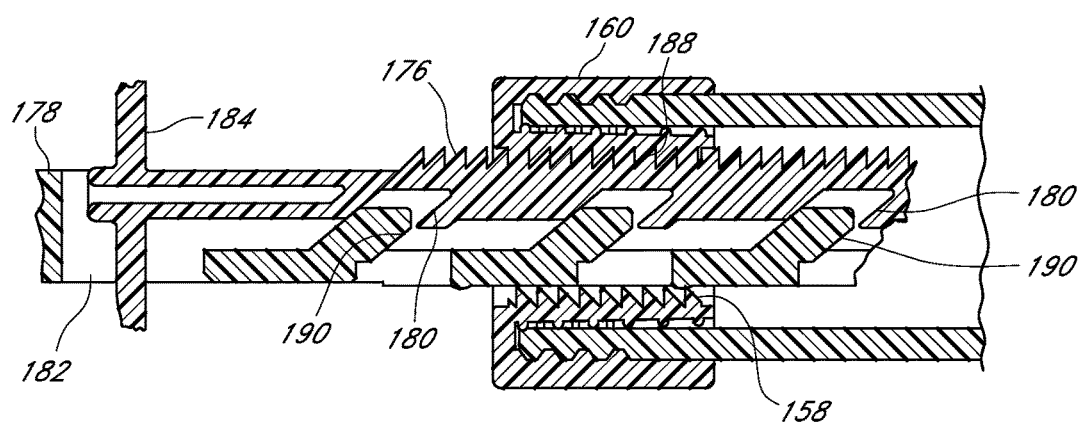
FIG. 4 is a cross-sectional view of the control mechanism of FIG. 3.
Figure 5:
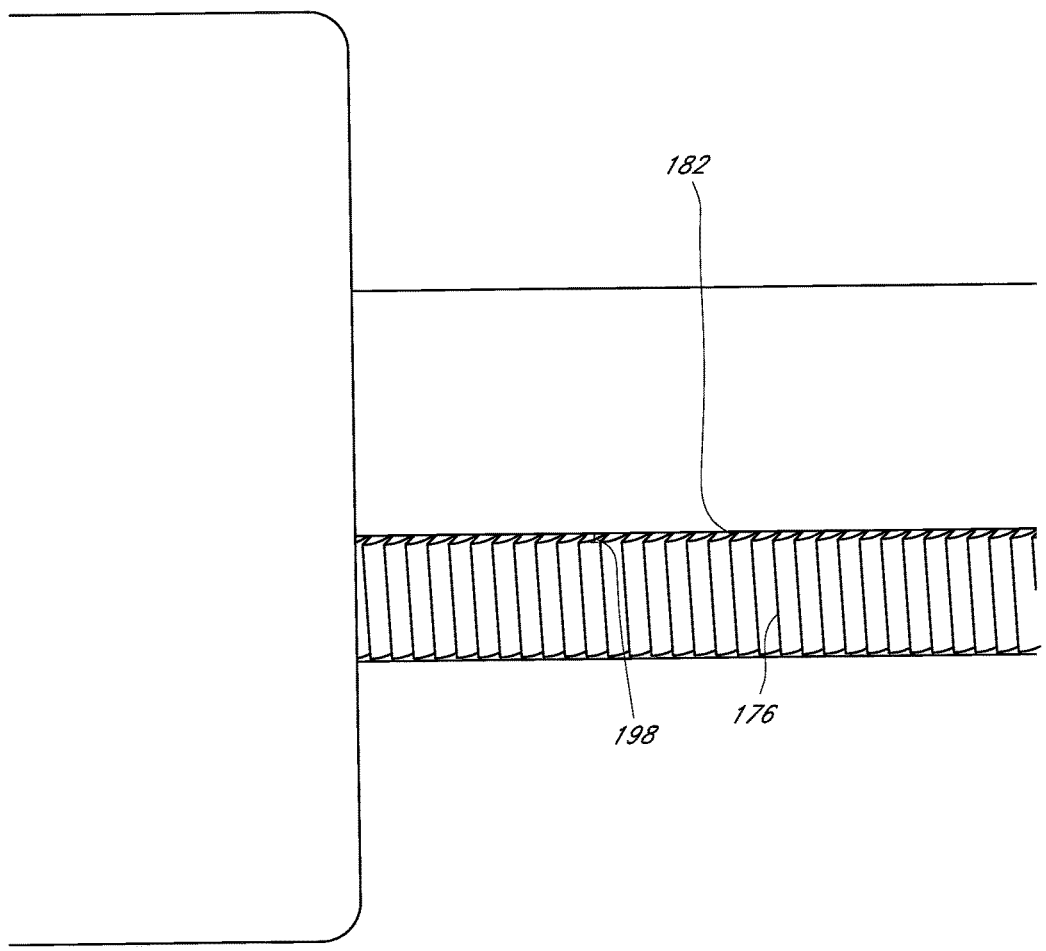
FIG. 5 is a perspective view of the control mechanism of FIG. 2 in a second position.
Figure 6:
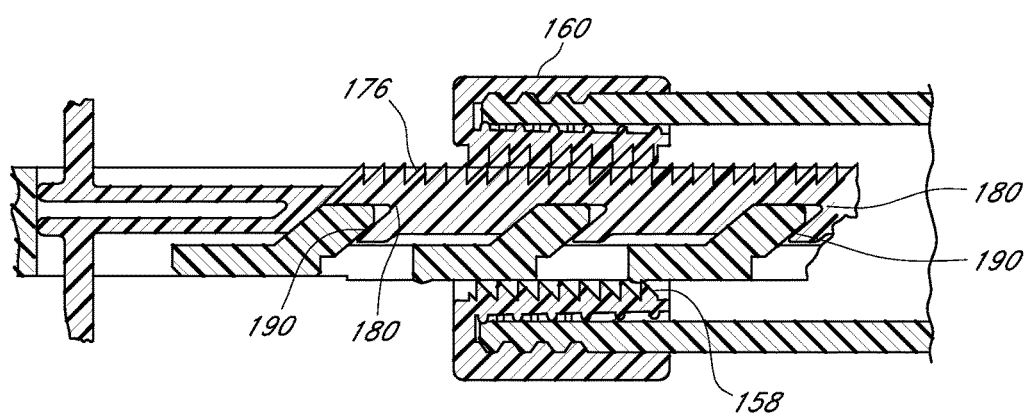
FIG. 6 is a cross-sectional view of the control mechanism of FIG. 5.

FIGS. 3-6 illustrate two possible positions of the inner core 184 with respect to the nut 160 and the outer sheath 178. FIGS. 3-4 shows inner core 184 disposed in a first position, such that the mating structure 176 are engaged with the complementary mating structure 158. FIGS. 5-6 shows inner core 184 disposed in a second position, such that the inner core 184 is sufficiently retracted into the outer sheath 176 that the mating structure 176 are not engaged with complementary mating structure 158.

The control mechanism 162 can be manually driven or motor-driven. In the embodiment of FIGS. 2-6, the control mechanism 162 is shown manually driven. The control mechanism 162 allows modulation of pressure or driving force. The handle 200 of the bone cement delivery system 100 may include components which enable a practitioner to engage or disengage the mating structure 176 and the complementary mating structure 158 (e.g., retract the inner core 184 of the elongate member 164).

In some embodiments, the outer sheath 178 may be fixed to an outer sheath handle 204. The inner core 184 may be fixed to an inner core handle 202. Further, a biasing component may bias the inner core handle 202 in a distal direction. Because the inner core handle 202 is fixed to the inner core 184, a distally oriented force on the inner core handle 202 will result in a distally oriented force on the inner core 184 as well. The force provided by the biasing component (hereafter referred to as the biasing force) may thus bias the inner core 184 as described herein. In this configuration, the control mechanism 162 can be in the first position. The inner core handle 202 and the outer sheath handle 204 can be rotate by the user when the control mechanism 162 is in the first position.

Conversely, overcoming the biasing force and translating the inner core handle 202 in a proximal direction with respect to the outer sheath handle 204 and outer sheath 178 may retract the inner core 184. In this configuration, the control mechanism 162 can be in the second position. In some embodiments, the user can squeeze the inner core handle 202 and the outer sheath handle 204. In some embodiments, the inner core handle 202 translates toward the outer sheath handle 204 when gripped. In other embodiments, the inner core handle 202 and the outer sheath handle 204 are brought together. This action causes the control mechanism 162 to transition from the first position to the second position. In other words, the user can manipulate the handle 200 to change the control mechanism 162 from the first position to the second position.

In some embodiments the handle 200 may further include one or more levers (not shown). The levers may be disposed such that they provide mechanical advantage, enabling the user to more easily overcome the biasing force and draw the inner core handle 202 toward the outer sheath handle 204.

It will be appreciated by one of ordinary skill in the art having the benefit of this disclosure that, in many instances, a proximal force will be applied to the inner core handle 202 at the same time a distal force is applied to the outer sheath handle 204. For example, when the handle 200 is grasped by a user, the user may actuate the handle 200 by squeezing the inner core handle 202 with his or her fingers. This action may coincide with a distally oriented force exerted on the outer sheath handle 204 by the palm of the user's hand. Accordingly, the forces applied in this manner may be understood as a proximal force on the inner core handle 202 and a distal force on the outer sheath handle 204. The mechanism of the levers essentially combines these forces into a single force acting to retract the inner core 184.

The relative distance between each contact point on the lever may create mechanical advantage, allowing a user to more easily overcome the biasing force and retract the inner core 178. Furthermore, any combination of these alternate designs is within the scope of this disclosure, including designs where each of two levers has a different design, the handle includes a single lever, or compliant mechanisms are utilized to perform transfer force and provide mechanical advantage.

Many design modifications relating to the outer sheath handle 204 are within the scope of the current disclosure. For example, in the illustrated embodiments, the outer sheath handle 204 has a cap-like shape, fitting over the inner core handle 202. In other embodiments, the outer sheath handle 204 may instead be designed as a button which slides into the inner core handle 202 when it is compressed. Likewise, any other longitudinally actuatable component may be utilized in place of the outer sheath handle 204.

The handle 202 may also be utilized to change the location and direction of an input force required to retract the mating structure 176. Essentially, the mechanism allows a user to draw the inner core handle 202 toward the outer sheath handle 204 (and thus retract the threads) solely by applying a distally oriented force to the top surface of the outer sheath handle 204. As outlined above, the levers transfer this force to the inner core handle 202 which retracts the mating structure 176.

In some instances a user, such as a medical practitioner, may desire to displace the elongate member 164 in a distal direction with only one hand. This may be accomplished by grasping the syringe body 156 and using a surface, for example a table top, to apply a distally oriented force on the top surface of the outer sheath handle 204. In this manner, a mechanism such as that described above may enable a practitioner to displace the elongate member 164 in a one-handed fashion. The force on the outer sheath handle 204 will both (1) retract the inner core 184 and the mating structure 176 via the handle 200 and (2) act to displace the elongate member 164 in a distal direction with respect to the syringe body 156. This orientation positions the syringe body 156 in a potentially desirable position to allow air bubbles in the fluid to travel to the distal end of the syringe body 156 while simultaneously orienting the handle 200 such that the top surface of the outer sheath handle 204 directly faces a horizontal surface such as a table. There may be other instances during therapy in which the practitioner desires to displace the elongate member 164 distally using only one hand.

In some instances the practitioner will displace the elongate member 164 as described after first retracting the mating structure 176. In some instances, the practitioner will do so by grasping the handle 200 with a first hand, while grasping the syringe body 156 with a second hand. The practitioner may then retract the inner core 184 by squeezing the inner core handle 202 and the outer sheath handle 204 together with his or her first hand, then drawing the elongate member 164. After a desired amount of fluid is disposed within the syringe body 156, the practitioner may orient the syringe body 156, so any air bubbles in the fluid will tend to rise to one end of the syringe body 156. The practitioner may also shake, tap, or otherwise disturb the syringe body 156 in order to facilitate movement of any air bubbles in the fluid.

FIG. 3-4 shows a perspective and cross-sectional view of the control mechanism 162 in the first position. In the first position, the inner core 184 is located closer to the cut out 182. The mating structure 176 extends through the cut out 182. The mating structure 176 extends a first distance 186 beyond the outer sheath 178. The mating structure 176 of the inner core 184 engages the complementary mating structure 158 of the proximal hydraulic fluid container 154.

In a method of operation in the first position, the elongate member 164 of the control mechanism 162 can be rotated. The wedges 188 act as a segment of a threaded rod. Rotation of the elongate member 164 causes rotation of the wedges 188. Similar to a threaded rod within a nut, rotation of the elongate member 164 will cause translation of the elongate member 164. Translating in a first direction 1 (e.g., distally) will cause the distal end 172 of the elongate member 164 to move further into the syringe body 156. This movement will cause the pressurized flow media 142 in the syringe body 156 to move from the proximal hydraulic fluid container 154 to the distal hydraulic fluid container 134 via the line 152. Further rotation of the elongate member 164 will cause more pressurized flow media 142 to move from the proximal hydraulic fluid container 154 to the distal hydraulic fluid container 134. The distal hydraulic fluid container 134 can be pressurized with flow media 148 by proximal hydraulic fluid container 154 to drive actuator member 132 distally toward the bone cement injector 102. The influx of pressurized flow media 142 will act upon the interface 146 between the actuator member 132 and the pressurized flow media 142, to thereby displace bone cement 128 from chamber 126 to the bone cement injector 102.

In some embodiments, a pressure application method of the invention can include one or more of the following steps (a) providing a proximal hydraulic fluid container with a displaceable fluid, (b) engaging a mating structure of the control mechanism with a complementary mating structure of the proximal hydraulic fluid container, (c) rotating the control mechanism to displace the fluid. In some embodiments, a pressure application method of the invention can include one or more of the following steps (a) providing a proximal hydraulic fluid container with a displaceable fluid, (b) engaging wedges of the control mechanism with a threaded bore of the proximal hydraulic fluid container, (c) rotating the control mechanism to displace the fluid.

Translating in a second direction 2 (e.g., proximally) will cause the distal end 172 of the elongate member 164 to move further out of the syringe body 156. This movement will cause the pressurized flow media 142 in the syringe body 156 to move from the distal hydraulic fluid container 134 to the proximal hydraulic fluid container 154 via the line 152. Further rotation of the elongate member 164 will cause more pressurized flow media 142 to move from the distal hydraulic fluid container 134 to the proximal hydraulic fluid container 154. The distal hydraulic fluid container 134 can be depressurized to drive actuator member 132 proximally away from the bone cement injector 102. However, this motion is incremental and the flow of bone cement 128 may continue to flow from the bone cement injector 102 even with depressurizing the distal hydraulic fluid container 134. The control mechanism 162 has a second position, which allows rapid translations of the elongate member 164 and rapid depressurization of the distal hydraulic fluid container 134.

In some instances, the practitioner may desire more precise control over the position of the elongate member 164 (for example when displacing the elongate member 164 in order to adjust the fluid pressure within the distal hydraulic fluid container 134) or it may simply be difficult or impossible without a mechanical advantage to displace the elongate member 164 due to high fluid pressure within the reservoir of the proximal hydraulic fluid container 154. In these instances, the practitioner may opt to displace the elongate member 164 by rotation of the elongate member 164.

FIG. 5-6 shows a perspective and cross-sectional view of the control mechanism 162 in the second position. In the second position, the inner core 184 is located further away from the cut out 182 than the first position. In some embodiments, the mating structure 176 extends only partially through the cut out 182. In some embodiments, the mating structure 176 does not extend through the cut out 182. The mating structure 176 extends a second distance 198 beyond the outer sheath 178, wherein the second distance 198 is less than the first distance 186. The mating structure 176 of the inner core 184 does not engage the complementary mating structure 158 of the proximal hydraulic fluid container 154. The wedges 188 can be retracted into the outer sheath 178. The wedges 188 can disengage the threaded bore 196. The elongate member 164 of the control mechanism 162 is free to translate within the proximal hydraulic fluid container 154.

In the second position, the elongate member 164 can translate in a first direction 1. The first direction 1 can be associated with pushing the distal end 172 further into the proximal hydraulic fluid container 154. The distal end 172 of elongate member 164 can displace pressurized flow media 142 from the proximal hydraulic fluid container 154 to the distal hydraulic fluid container 134. In this mode of operation, the user can rapidly displace bone cement 128 by moving the elongate member in the first direction 1. This can permit faster displacement of flow media 142 in the second position than the displacement of flow media 142 in the first position. This can permit a greater volume of displacement of flow media 142 in the second position than the displacement of flow media 142 in the first position. For instance, a push of the elongate member 164 may displace a larger volume of bone cement (e.g., 2 mL, 3 mL, 4 mL, 5 mL) as compared to a full rotation in the first position (e.g., 0.5 mL, 1 mL, 1.5 mL, 2 mL).

This movement in the first direction 1 will cause the pressurized flow media 142 in the syringe body 156 to rapidly move from the proximal hydraulic fluid container 154 to the distal hydraulic fluid container 134 via the line 152. Further translation of the elongate member 164 will cause more pressurized flow media 142 to move from the proximal hydraulic fluid container 154 to the distal hydraulic fluid container 134. The distal hydraulic fluid container 134 can be pressurized with flow media 148 by proximal hydraulic fluid container 154 to drive actuator member 132 distally. The influx of pressurized flow media 142 will act upon the interface 146 between the actuator member 132 and the pressurized flow media 142, to thereby displace bone cement 128 from chamber 126 to the bone cement injector 102.

The elongate member 164 can translate in a second direction 2. This motion can rapidly displace pressurized flow media 142 from the distal hydraulic fluid container 134 to the proximal hydraulic fluid container 154. The second direction 2 can be associated with pulling the distal end 172 further out of the proximal hydraulic fluid container 154. The distal end 172 of elongate member 164 can displace pressurized flow media 142 from the distal hydraulic fluid container 134 to the proximal hydraulic fluid container 154. In this mode of operation, the user can retract bone cement 128 back into the chamber 126 in the syringe body 124. In this mode of operation, the user can stop the flow of bone cement 128 from the bone cement injector 102.

In some instances, a practitioner may desire to quickly displace the elongate member 164, for instance, while priming the bone cement delivery system 100. Quick displacement of the elongate member 164 may be accomplished by retracting the inner core 184 and sliding the elongate member 164 relative to the syringe body 156. For example, a practitioner may quickly fill the reservoir of the proximal hydraulic fluid container 154 with flow media 142 by disengaging the mating structure 176 and pulling the elongate member 164 in a proximal direction with respect to the syringe body 156. Further, a practitioner may quickly force flow media 142 into the line 152 leading to the distal hydraulic fluid container 134 or quickly expel unwanted air bubbles from the reservoir of the proximal hydraulic fluid container 154 by retracting the inner core 187 and repositioning the elongate member 164.

In some embodiments, a pressure application method of the invention can include one or more of the following steps (a) providing a proximal hydraulic fluid container with a displaceable fluid, (b) disengaging a mating structure of the control mechanism with a complementary mating structure of the proximal hydraulic fluid container, (c) translating the control mechanism to displace the fluid. In some embodiments, a pressure application method of the invention can include one or more of the following steps (a) providing a proximal hydraulic fluid container with a displaceable fluid, (b) disengaging wedges of the control mechanism with a threaded bore of the proximal hydraulic fluid container, (c) translating the control mechanism to displace the fluid.

In some embodiments, a pressure application method of the invention can include one or more of the following steps (a) providing a proximal hydraulic fluid container and a distal hydraulic fluid container with a displaceable fluid, (b) disengaging a mating structure of the control mechanism with a complementary mating structure of the proximal hydraulic fluid container, (c) translating the control mechanism to displace the fluid from the distal hydraulic fluid container to the proximal hydraulic fluid container. In some embodiments, a pressure application method of the invention can include one or more of the following steps (a) providing a proximal hydraulic fluid container and a distal hydraulic fluid container, (b) disengaging a mating structure of the control mechanism with a complementary mating structure of the proximal hydraulic fluid container, (c) translating the control mechanism release pressure of the distal hydraulic fluid container.

In some embodiments, a pressure application method of the invention can include one or more of the following steps (a) providing a proximal hydraulic fluid container and a distal hydraulic fluid container with a displaceable fluid, (b) disengaging wedges of the control mechanism with a threaded bore of the proximal hydraulic fluid container, (c) translating the control mechanism to displace the fluid from the distal hydraulic fluid container to the proximal hydraulic fluid container. In some embodiments, a pressure application method of the invention can include one or more of the following steps (a) providing a proximal hydraulic fluid container and a distal hydraulic fluid container, (b) disengaging wedges of the control mechanism with a threaded bore of the proximal hydraulic fluid container, (c) translating the control mechanism release pressure of the distal hydraulic fluid container.

The bone cement delivery system 100 can have a default position, which may be the first position or the second position. In the illustrated embodiment, the default position is the first position. Therefore, the mating structure 176 of the inner core 184 will engage the complementary mating structure 158 of the proximal hydraulic fluid container 154. In the first position, the elongate member 164 of the control mechanism can be rotated to incrementally displace pressurized flow media 142.

The bone cement delivery system 100 can have a third position. The third position of the bone cement delivery system 100 can prevent the flow of bone cement from the bone cement injector 102. In both the first and second position described above, the stopcock 136 is closed to allow the flow media 142 to travel between the distal hydraulic fluid container 134 and the proximal hydraulic fluid container 154. In the third position, the stopcock 136 is actuated to prevent the flow media 142 to travel between the distal hydraulic fluid container 134 and the proximal hydraulic fluid container 154. In some embodiments, the stopcock 136 is actuated to allow the flow media 142 to travel through an opening 140. The flow media 142 can be expelled (e.g., into air) or captured in a container (not shown).

The third position allows pressure to be released immediately in the distal hydraulic fluid container 134. This position can rapidly displace pressurized flow media 142 from the distal hydraulic fluid container 134 and/or the proximal hydraulic fluid container 154. The stopcock 136 can be coupled to the proximal end of the distal hydraulic fluid container 134 and allow for rapid release of pressure in the distal hydraulic fluid container 134. The stopcock 136 can be coupled to the end of the proximal hydraulic fluid container 154 and allow for rapid release of pressure in the proximal hydraulic fluid container 154. In this mode of operation, the user can retract bone cement 128 back into the chamber 126 in the syringe body 124. In this mode of operation, the user can stop the flow of bone cement 128 from the bone cement injector 102. The stopcock 136 provides an alternative to the second position for rapidly decreasing the pressure in the distal hydraulic fluid container 134 and/or the proximal hydraulic fluid container 154. The stopcock 136 and the control mechanism 162 provide the ability to have different actuators to change the pressure in the distal hydraulic fluid container 162.

The bone cement delivery system 100 can include the mechanisms associated with one or more of the three positions. For instance, in some embodiments bone cement delivery system 100 can operate in the first position and the third position, but not the second position. This bone cement delivery system 100 can includes the stopcock 136, the mating structures 176 and the complementary mating structure 158, but not the mechanism that permits the retraction or advancement of the inner core 184. For instance, in some embodiments bone cement delivery system 100 can operate in the first position and the second position, but not the third position. This bone cement delivery system 100 can exclude the stopcock 136.

In some embodiments, a pressure application method of the invention can include one or more of the following steps (a) providing a distal hydraulic fluid container and a proximal hydraulic fluid container with a displaceable fluid, (b) activating a valve to prevent the flow of the fluid between the distal hydraulic fluid container and the proximal hydraulic fluid container, (c) releasing the pressure in the distal hydraulic fluid container and/or the proximal hydraulic fluid container. In some embodiments, a pressure application method of the invention can include one or more of the following steps (a) providing a distal hydraulic fluid container and a proximal hydraulic fluid container with a displaceable fluid, (b) opening a stopcock to prevent the flow of the fluid between the distal hydraulic fluid container and the proximal hydraulic fluid container, (c) expelling the fluid from the distal hydraulic fluid container and/or the proximal hydraulic fluid container.

In some embodiments, a pressure application method of the invention can include one or more of the following steps (a) providing a distal hydraulic fluid container and a proximal hydraulic fluid container with a displaceable fluid, (b) closing or providing a closed valve to permit the flow of the fluid between the distal hydraulic fluid container and the proximal hydraulic fluid container; (c) opening the valve to prevent the flow of the fluid between the distal hydraulic fluid container and the proximal hydraulic fluid container.

In some embodiments, a pressure application method of the invention can include one or more of the following steps (a) providing a distal hydraulic fluid container and a proximal hydraulic fluid container with a displaceable fluid, (b) closing or providing a closed valve to permit the flow of the fluid between the distal hydraulic fluid container and the proximal hydraulic fluid container; (c) engaging a mating structure of the control mechanism with a complementary mating structure of the proximal hydraulic fluid container, (d) rotating the control mechanism to displace the fluid, (e) opening the valve to prevent the flow of the fluid between the distal hydraulic fluid container and the proximal hydraulic fluid container.

In some embodiments, a pressure application method of the invention can include one or more of the following steps (a) providing a distal hydraulic fluid container and a proximal hydraulic fluid container with a displaceable fluid, (b) closing or providing a closed valve to permit the flow of the fluid between the distal hydraulic fluid container and the proximal hydraulic fluid container; (c) engaging a mating structure of the control mechanism with a complementary mating structure of the proximal hydraulic fluid container, (d) rotating the control mechanism to displace the fluid, (e) disengaging a mating structure of the control mechanism with a complementary mating structure of the proximal hydraulic fluid container, (f) translating the control mechanism to displace the fluid, and optionally (g) opening the valve to prevent the flow of the fluid between the distal hydraulic fluid container and the proximal hydraulic fluid container.

In some embodiments, a pressure application method of the invention can include one or more of the following steps (a) providing a distal hydraulic fluid container and a proximal hydraulic fluid container with a displaceable fluid, (b) closing or providing a closed valve to permit the flow of the fluid between the distal hydraulic fluid container and the proximal hydraulic fluid container; (c) engaging wedges of the control mechanism with a threaded bore of the proximal hydraulic fluid container, (e) rotating the control mechanism to displace the fluid, (e) disengaging wedges of the control mechanism with a threaded bore of the proximal hydraulic fluid container, (f) translating the control mechanism to displace the fluid, and optionally (g) opening the valve to prevent the flow of the fluid between the distal hydraulic fluid container and the proximal hydraulic fluid container.

FIGS. 7-10 show a schematic view of the bone cement delivery system 100 of FIGS. 2-6. FIG. 7 shows the system used to inject bone cement 128 into a vertebral body. The trocar described herein can be used to puncture a hole into the vertebral body. The bone cement injector 102 can be inserted into the vertebral body. The bone cement delivery system 100 includes a chamber 126 for bone cement 128, the actuator member 132, and the distal hydraulic fluid container 134 as described herein. The distal hydraulic fluid container 134 and the proximal hydraulic fluid container 154 include flow media 142. The distal hydraulic fluid container 134 is connected to the proximal hydraulic fluid container via line 152 and the stopcock 136. The stopcock 136 is closed to allow the flow media 142 to travel between the distal hydraulic fluid container 134. The proximal hydraulic fluid container 154 received the distal end 172 of the elongate member 164. The control mechanism is coupled to the handles 202, 204 to retract the mating structure 176. The bone cement delivery system 100 can optionally include a pressure gauge for measuring injection pressure.

FIG. 8 shows the relative pressures and viscosities of the bone cement delivery system 100. The distal hydraulic fluid container 134 has a first viscosity V1 and a first pressure P1. The chamber 126 has a second viscosity V2 and a second pressure P2. The first pressure P1 and the second pressure P2 are equal. The first viscosity V1 and the second viscosity V2 can be unequal. The proximal hydraulic fluid container 154 has a first viscosity V1 and a first pressure P1.

FIG. 9A shows the stopcock 136 in the closed configuration. In both the first and second position described above, the stopcock 136 is closed to allow the flow media 142 to travel between the distal hydraulic fluid container 134 and the proximal hydraulic fluid container 154. The distal hydraulic fluid container 134 has the first viscosity V1 and the first pressure P1. The chamber 126 has a second viscosity V2 and a second pressure P2, wherein P2 is equal to P1. The viscosity of the bone cement V2 may be greater than the viscosity of the flow media 142.

FIG. 9B shows the stopcock 136 in the open configuration. In the third position, the stopcock 136 is opened to prevent the flow media 142 to travel between the distal hydraulic fluid container 134 and the proximal hydraulic fluid container 154. In some embodiments, the stopcock 136 is opened to allow the flow media 142 to travel through an opening 140. The flow media 142 can be expelled (e.g., into air) or captured in a container (not shown). The flow of high viscosity (V2) bone cement 128 halts and there is preferential flow to lower viscosity V1. In some instances, if pressure is released from the distal hydraulic fluid container 134 slowly (e.g., rotation to release pressure in the first position), the bone cement may continue to flow. The third position allows the bone cement delivery system 100 to rapidly stop the flow of bone cement 128.

Figure 10:
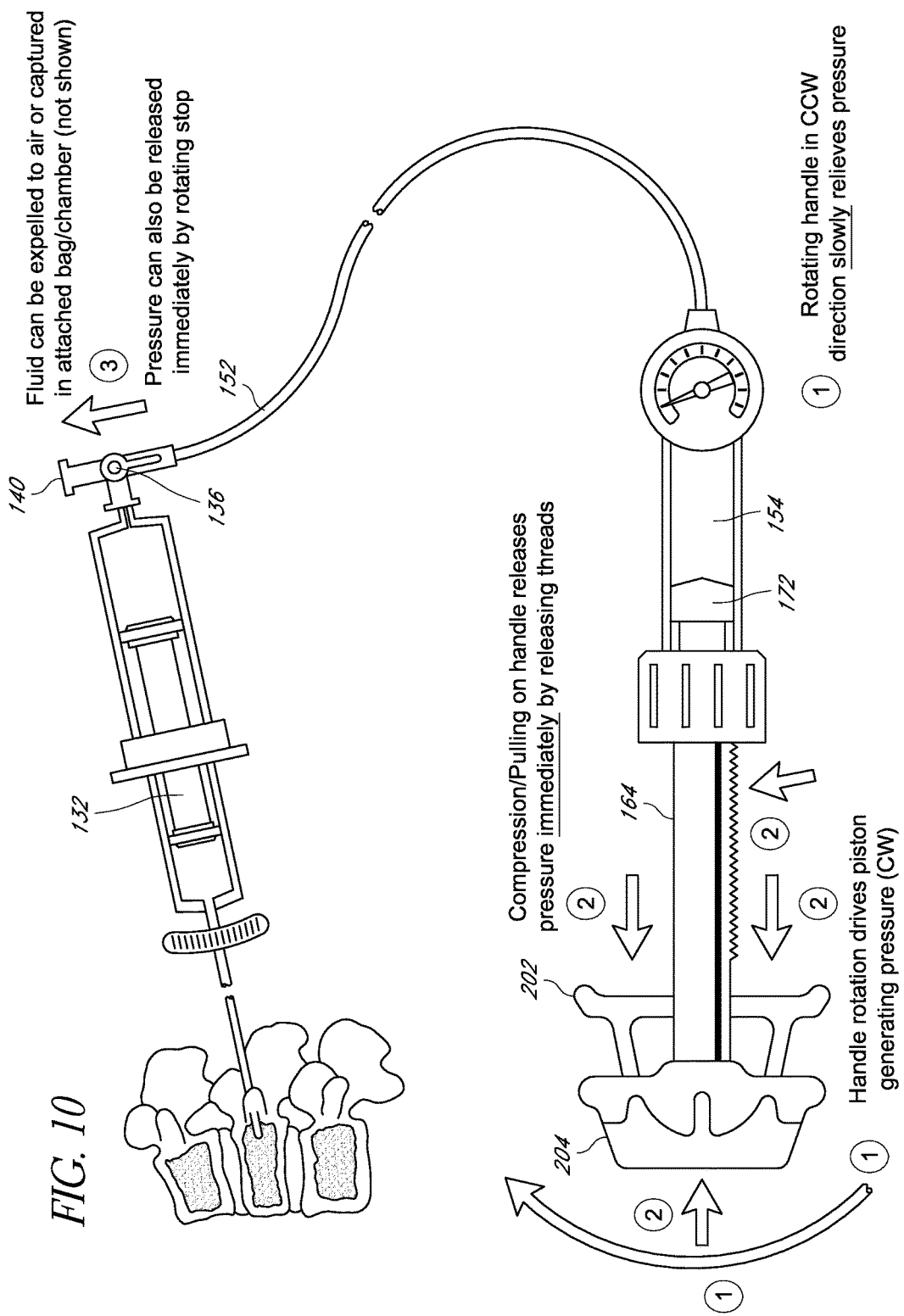
FIG. 10 is a schematic view of the of the injection system of FIG. 2.

FIG. 10 show the three positions of the bone cement delivery system 100. In the first position, the handles 202, 204 are rotated to move the distal end 172 within the proximal hydraulic fluid container 154. The mating structure engages the complementary mating structure. The clockwise rotation generates pressure in the proximal hydraulic fluid container 154, which generates pressure in the distal hydraulic fluid container 134, and which drives the actuator member 132 to advance the bone cement. The counterclockwise rotation slowly relieves pressure in the proximal hydraulic fluid container 154, which slowly relieves pressure in the distal hydraulic fluid container 134, and which may retract the actuator member 132 to prevent the flow of the bone cement 128. In the second position, the handles 202, 204 are translated to move the distal end 172 within the proximal hydraulic fluid container 154. The mating structure disengages the complementary mating structure. In the second position, the compression and/or pulling on the handles 202, 204 disengages the mating structure and the complementary mating structure. The pressure can be immediately released by pulling the elongate member 164 out of the proximal hydraulic fluid container 154. The motion rapidly relieves pressure in the proximal hydraulic fluid container 154, which rapidly relives pressure in the distal hydraulic fluid container 134, and which may retract the actuator member 132 to prevent the flow of the bone cement 128. In the third position, the stopcock 136 is opened. In the third embodiment, the fluid can be expelled to the air or captured in an attached bag or container (not shown). The opening of the stopcock 136 rapidly relieves pressure in the distal hydraulic fluid container 134 and the proximal hydraulic fluid container 154, which may retract the actuator member 132 to prevent the flow of the bone cement 128.

Figure 11:
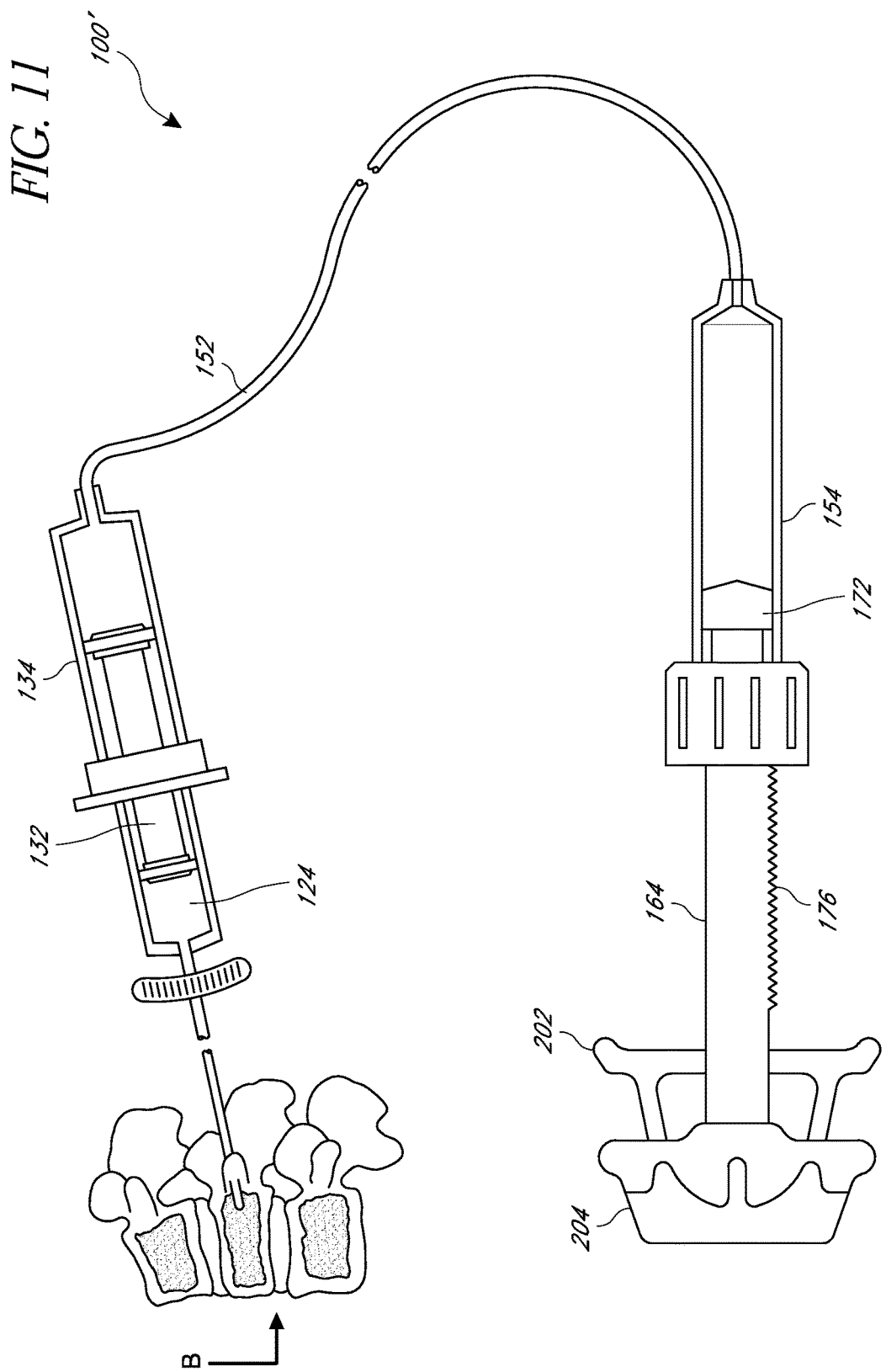
FIG. 11 is a schematic view of one embodiment of an injection system for delivering bone cement into a bone.
Figure 12:
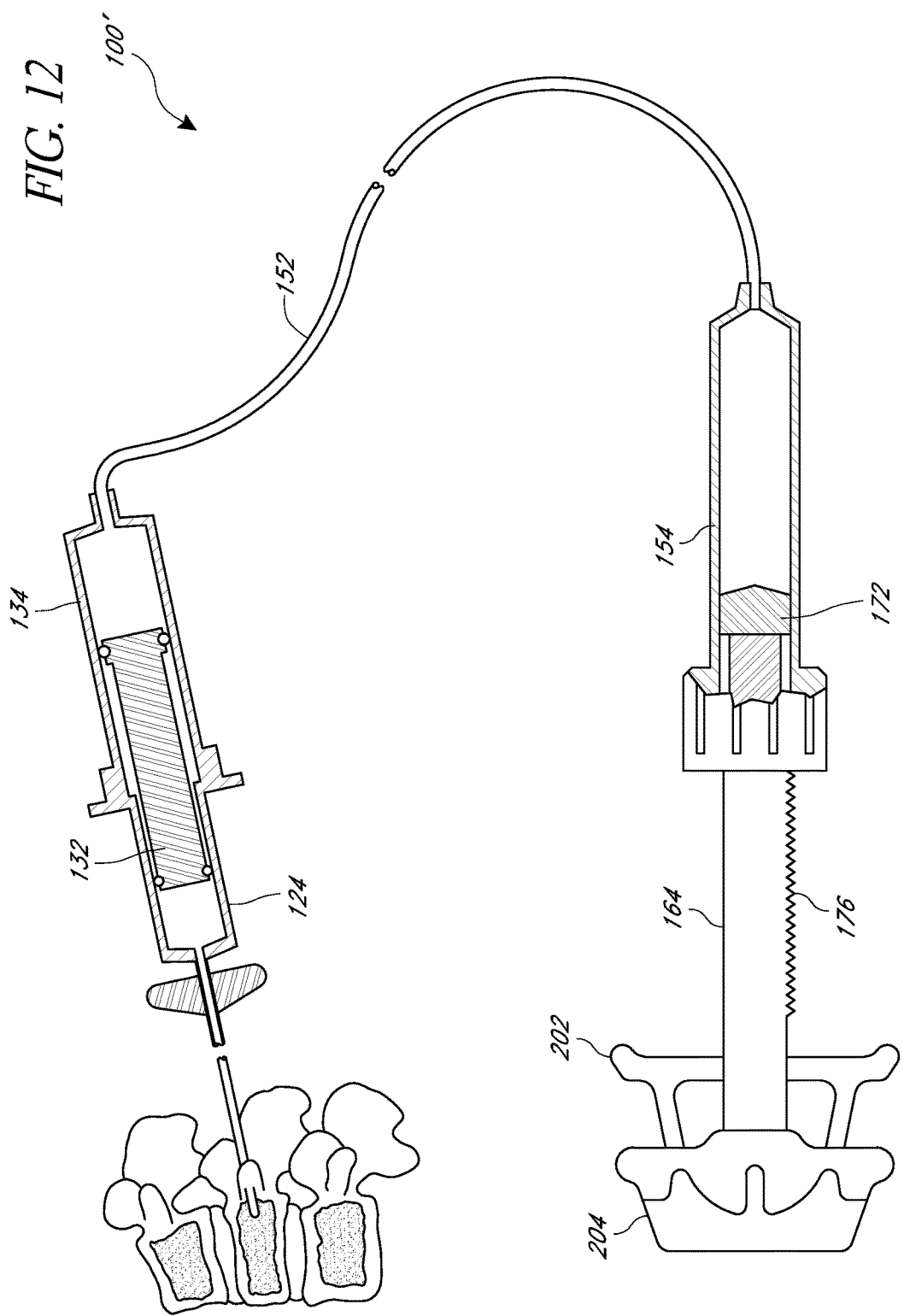
FIG. 12 is a schematic view of the injection system in FIG. 11 showing some components in cross-section.

The mating structure 176 of the inner core 184 with the complementary mating structure 158 of the proximal hydraulic fluid container 154 can have a different configuration than the embodiment of FIGS. 2-6. FIGS. 11-12 illustrate one embodiment of the control mechanism 162. The control mechanism 162 has a first position and a second position. The first position is associated with incremental movement of the pressurized flow media 142. The first position allows incremental increases or decreases in pressure between the proximal hydraulic fluid container 154 and the distal hydraulic fluid container 134. The second position allows rapid increases or decreases in pressure between the proximal hydraulic fluid container 154 and the distal hydraulic fluid container 134.

FIGS. 11-12 show another embodiment of an injection system 100' for delivering bone cement into a bone. The injection system 100' is identical to the system 100 shown in FIGS. 7-8 except as described below. Thus, the reference numerals used to designate the various components of the system 100' are identical to those used for identifying the corresponding components of the system 100 in FIGS. 7-8, except as noted below. In the illustrated embodiment, the system 100' does not have a pressure gauge or regulator. Additionally, the system 100' does not have a stopcock between the line 152 and the distal hydraulic fluid container 134.

Figure 13:
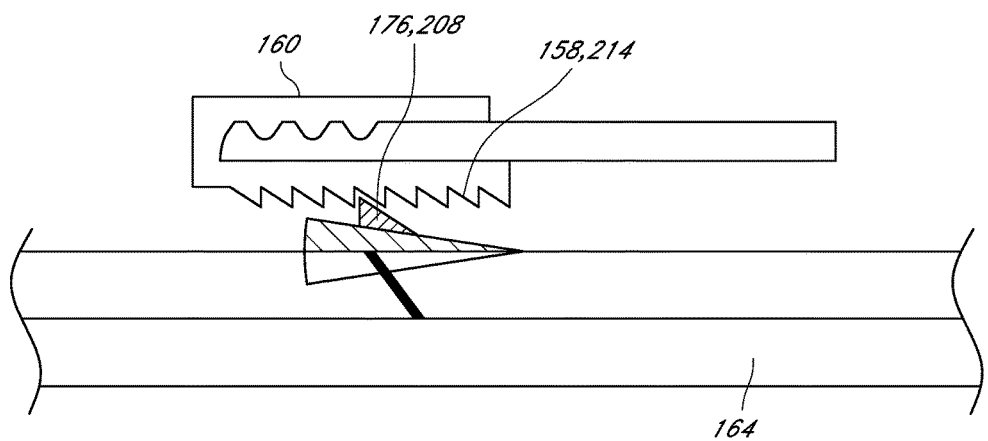
FIG. 13 is a cross-sectional view of one embodiment of a control mechanism in a first position.
Figure 14:
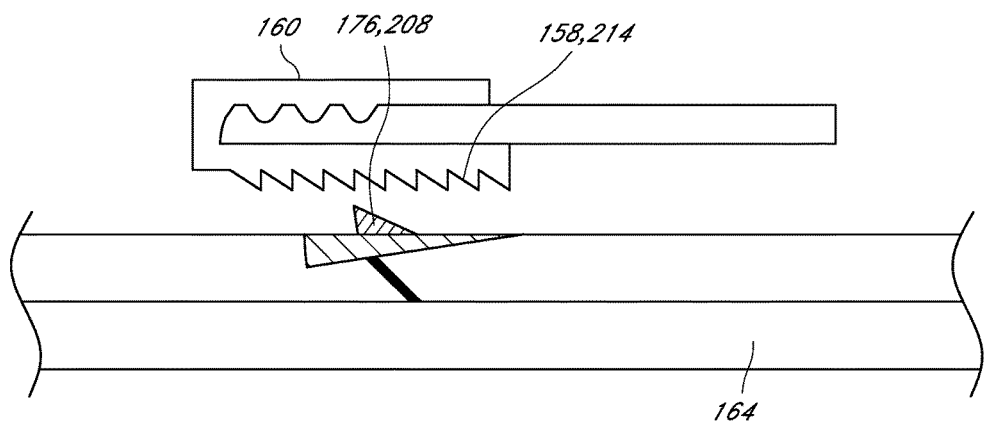
FIG. 14 is a cross-sectional view of one embodiment of a control mechanism in a second position.

FIG. 13 shows the control mechanism 162 in the first position and FIG. 14 shows the control mechanism 162 in the second position. In the illustrated embodiment, the mating structure 176 of the elongate member 164 is a pawl 208. The pawl 208 can have a substantially ramped surface 212. The substantially ramped surface 212 may allow the pawl 208 to engage the complementary mating structure 158. The pawl 208 can extend along a portion of the elongate member 164, such as a distal portion of the elongate member 164. In some embodiments, the retraction or advancement of the pawl 208 causes the control mechanism 162 to change from the first position to a second position.

In some embodiments, the elongate member 164 includes an outer sheath 178 having one or more cut outs 182. The elongate member 164 includes an inner core 184. The inner core 184 includes the pawl 208. The inner core 184 is disposed within the outer sheath 178. The inner core 184 can be sized to permit movement within the outer sheath 178. In some embodiments, the inner core 184 can translate from a first position to a second position. The pawl 208 has a width less than or equal to the width of the cut out 182. The pawl 208 is sized to extend from the cut out 182 of the outer sheath 178.

In the illustrated embodiment, the complementary mating structure 158 of the proximal hydraulic fluid container 154 is ratchet 214 disposed within a bore 216. The elongate member 162 can have a similar diameter as the bore 216. The ratchet 214 permits incremental changes in fluid displacement. For instance, advancing one tooth on the ratchet 214 may only displace a small volume of bone cement (e.g., 0.5 mL, 1 mL, 1.5 mL, 2 mL). Further the ratchet 214 and the pawl 208 may prevent the disengagement between the elongate member 164 and the proximal hydraulic fluid container 154. The translational movement of the ratchet 214 and pawl 208 in the first position can be faster than the translational movement of the wedges 188 within the threaded bore 198 in the first position.

In some embodiments, the mating structure 176 of the inner core 184 can have two pawls and the complementary mating structure of the proximal hydraulic fluid container 154 can have two ratchets 214 disposed within a bore 216. The first pawl 208 and the first ratchet 214 can be substantially similar to the pawl 208 and ratchet 214 shown in FIG. 7. The second pawl 208 and ratchet 214 can be disposed at another circumferential location, such as offset by 180 degrees (not shown). The second pawl 208 and ratchet 214 can be disposed at another distance along the axis 174. The second pawl can provide a second point of contact between the mating structure 176 of the inner core 184 and the complementary mating structure 158 of the proximal hydraulic fluid container 154. In some embodiments, the two pawls 208 can be simultaneously retracted in the second position. In some embodiments, each pawl 208 is independently retracted in the second position.

In some embodiments, the user can squeeze the inner core handle 202 and the outer sheath handle 204. In some embodiments, the inner core handle 202 translates toward the outer sheath handle 204. In other embodiments, the inner core handle 202 and the outer sheath handle 204 are brought together. This action causes control mechanism 162 to transition from the first position to the second position. In other words, the user can manipulate the inner core handle 202 to disengage the pawl 208 of the inner core 184 with the ratchet 214 of the proximal hydraulic fluid container 154.

In some embodiments, the pawl 208 is disposed on the surface of the elongate member 164. The elongate member 164 can include a handle 222 which retracts the pawl. The retraction of the pawl 208 causes the control mechanism 162 to change from the first position to the second position.

In above examples, the mating structure 176 can be associated with the proximal hydraulic fluid container 154 and the complementary mating structure 158 can be associated with the elongate member 164. For instance, in some embodiments, the mating structure 176 of the elongate member 164 is a ratchet 214. The complementary mating structure 158 of the proximal hydraulic fluid container 154 is a pawl 208 disposed within a bore 216. In some embodiments, the mating structure 176 of the elongate member 164 includes one or more ratchets 214 and the complementary mating structure 158 of the proximal hydraulic fluid container 154 includes one or more pawls 208. The proximal hydraulic fluid container 154 can include a handle 218 which retracts the pawl 208. The retraction of the pawl 208 causes the control mechanism 162 to change from the first position to the second position.

The control mechanism 162 has the first position shown in FIG. 7 and the second position shown in FIG. 8. The first position is associated with incremental movement of the pressurized flow media 142. The first position allows incremental increases in pressure between the proximal hydraulic fluid container 154 and the distal hydraulic fluid container 134. The second position allows rapid increases or decreases in pressure between the proximal hydraulic fluid container 154 and the distal hydraulic fluid container 134.

In a method of operation in the first position, the elongate member 164 of the control mechanism 162 can be translated. The elongate member 164 can translate in a first direction 1. The first direction 1 can be associated with pushing the distal end 172 further into the proximal hydraulic fluid container 154. The movement in the first direction 1 will cause the pressurized flow media 142 in the syringe body 156 to move from the proximal hydraulic fluid container 154 to the distal hydraulic fluid container 134 via the line 152. Further translation of the elongate member 164 will cause more pressurized flow media 142 to move from the proximal hydraulic fluid container 154 to the distal hydraulic fluid container 134. The distal hydraulic fluid container 134 can be pressurized with flow media 148 by proximal hydraulic fluid container 154 to drive actuator member 132 distally. The influx of pressurized flow media 142 will act upon the interface 146 between the actuator member 132 and the pressurized flow media 142, to thereby displace bone cement 128 from chamber 126 in the syringe body 124. In some embodiments, a pressure application method of the invention can include one or more of the following steps (a) providing a proximal hydraulic fluid container with a displaceable fluid, (b) engaging a pawl of the control mechanism with a ratchet of the proximal hydraulic fluid container, (c) translating the control mechanism to displace the fluid.

In the first position, the ratchet 214 can permit movement in a first direction 1 and prohibit movement in a second direction 2. This prevents the displacement of pressurized flow media 142 from the distal hydraulic fluid container 134 to the proximal hydraulic fluid container 154. The second direction 2 can be associated with pulling the distal end 172 further out of the proximal hydraulic fluid container 154.

In the second position, the elongate member 164 can translate in a first direction 1 and the second direction 2. The first direction movement is described above. The elongate member 164 can translate in a second direction 2. This motion can rapidly displace pressurized flow media 142 from the distal hydraulic fluid container 134 to the proximal hydraulic fluid container 154. The second direction 2 can be associated with pulling the distal end 172 further out of the proximal hydraulic fluid container 154. The distal end 172 of elongate member 164 can displace pressurized flow media 142 from the distal hydraulic fluid container 134 to the proximal hydraulic fluid container 154. In this mode of operation, the user can retract bone cement 128 back into the chamber 126 in the syringe body 124. In this mode of operation, the user can stop the flow of bone cement 128 from the bone cement injector 102.

The bone cement delivery system 100 can have a third position. The third position of the bone cement delivery system 100 can prevent the flow of bone cement from the bone cement injector 102. In both the first and second position described above, the stopcock 136 is closed to allow the flow media 142 to travel between the distal hydraulic fluid container 134 and the proximal hydraulic fluid container 154. In the third position, the stopcock 136 is opened to prevent the flow media 142 to travel between the distal hydraulic fluid container 134 and the proximal hydraulic fluid container 154. In some embodiments, the stopcock 136 is opened to allow the flow media 142 to travel through an opening 140. The flow media 142 can be expelled (e.g., into air) or captured in a container (not shown). In this mode of operation, the user can retract bone cement 128 back into the chamber 126 in the syringe body 124. In this mode of operation, the user can stop the flow of bone cement 128 from the bone cement injector 102. The stopcock 136 provides an alternative to the second position for rapidly decreasing the pressure in the distal hydraulic fluid container 134 and/or the proximal hydraulic fluid container 154. The stopcock 136 and the control mechanism 162 provide the ability to have different actuators to change the pressure in the distal hydraulic fluid container 162. The bone cement delivery system 100 can include the mechanisms associated with one or more of the three positions.

In some embodiments, a pressure application method of the invention can include one or more of the following steps (a) providing a distal hydraulic fluid container and a proximal hydraulic fluid container with a displaceable fluid, (b) closing or providing a closed valve to permit the flow of the fluid between the distal hydraulic fluid container and the proximal hydraulic fluid container; (c) engaging a mating structure of the control mechanism with a complementary mating structure of the proximal hydraulic fluid container, (d) translating the control mechanism to displace the fluid, (e) opening the valve to prevent the flow of the fluid between the distal hydraulic fluid container and the proximal hydraulic fluid container.

In some embodiments, a pressure application method of the invention can include one or more of the following steps (a) providing a distal hydraulic fluid container and a proximal hydraulic fluid container with a displaceable fluid, (b) closing or providing a closed valve to permit the flow of the fluid between the distal hydraulic fluid container and the proximal hydraulic fluid container; (c) engaging a pawl of the control mechanism with a ratchet of the proximal hydraulic fluid container, (d) translating the control mechanism to displace the fluid, (e) disengaging a pawl of the control mechanism with a ratchet of the proximal hydraulic fluid container, (f) translating the control mechanism to displace the fluid, and optionally (g) opening the valve to prevent the flow of the fluid between the distal hydraulic fluid container and the proximal hydraulic fluid container.

Figure 15:
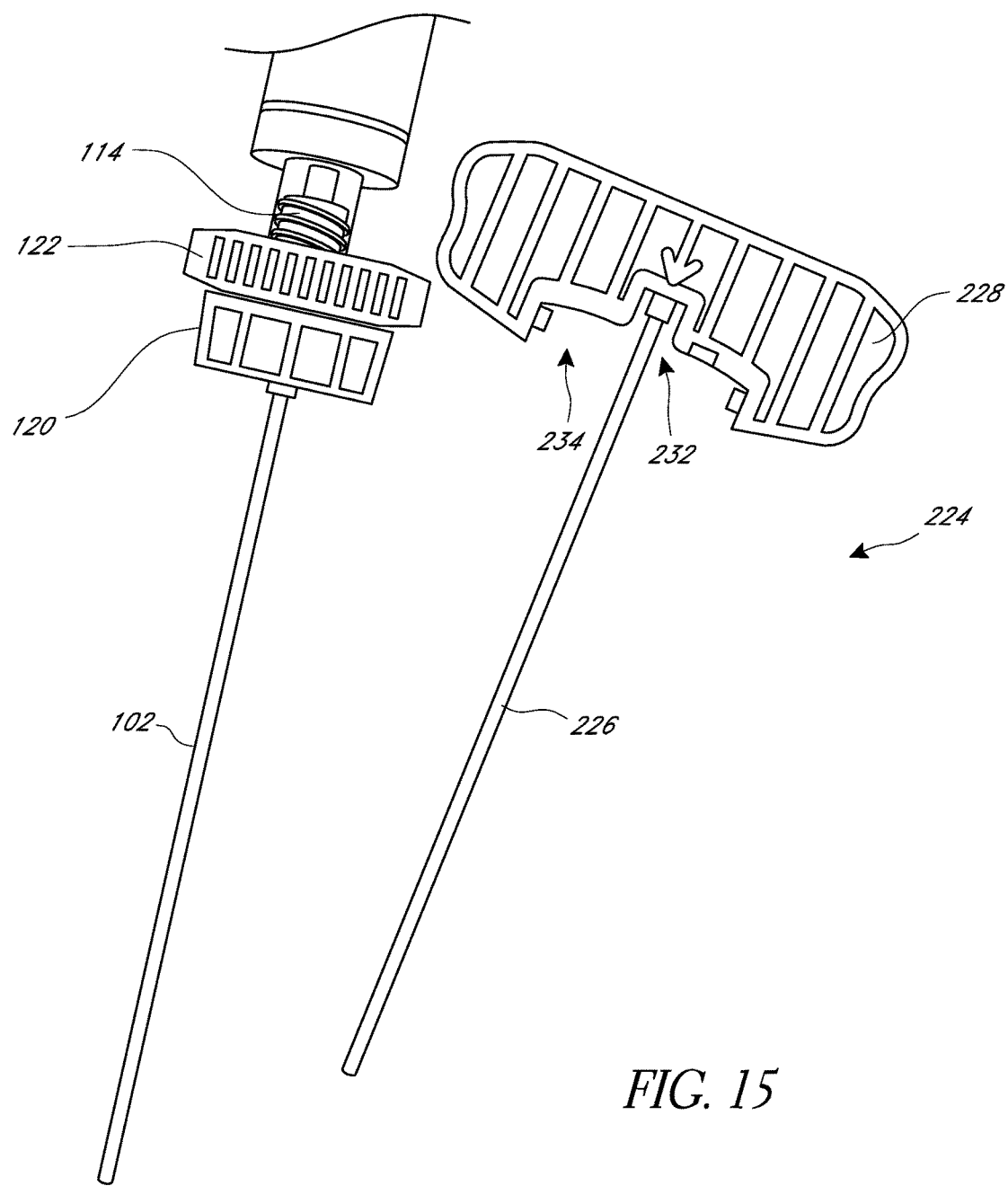
FIG. 15 is a perspective view of a trocar and the injection system of FIG. 2.
Figure 16:
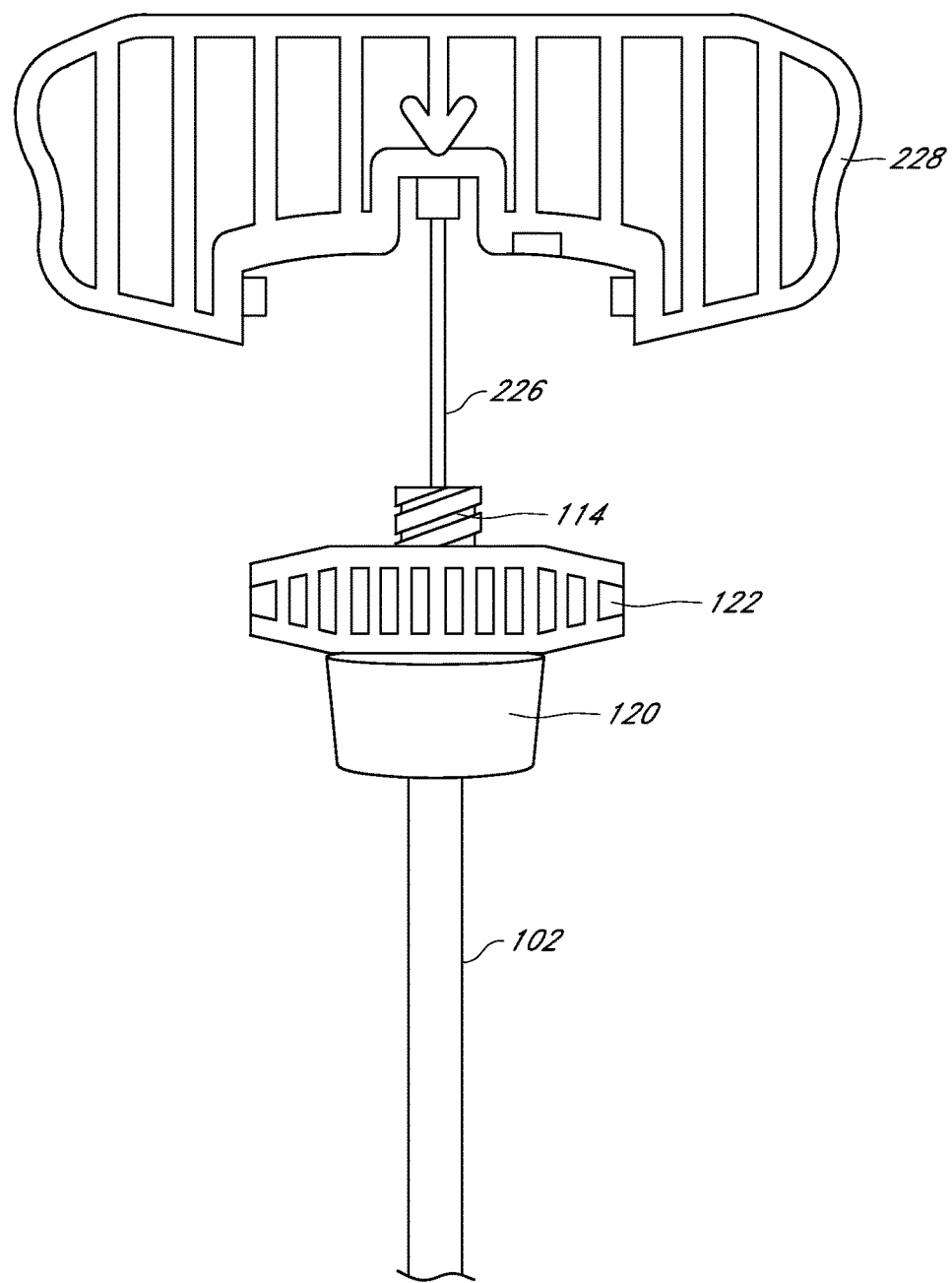
FIG. 16 is a perspective view of the trocar of FIG. 15.

FIGS. 15-16 show an embodiment of a trocar 224 which may be used with the bone cement delivery system 100. The trocar 224 includes an elongate shaft 226 sized to fit within the flow channel of the bone cement injector 102. The trocar 224 includes a handle 228 to facilitate gripping the trocar 224. The fitting 114 of the bone cement injector 102 is sized to nest within a cut out 232 the handle 228. The bar 122 of the bone cement injector 102 is sized to nest within a second cut out 234 of the handle.

The systems described herein advantageously provide multiple mechanisms for releasing pressure (e.g., in the proximal and distal hydraulic fluid containers) to cease or prevent continued flow of bone cement through the injector cannula, which provides the practitioner with flexibility on whether to release pressure relatively slowly or relatively quickly, as well as the location at with said pressure is released (e.g., at the proximal end near the proximal hydraulic fluid container, or distally near the distal hydraulic fluid container).

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for delivering bone cement into a bone, comprising:

a bone cement injector extending along a longitudinal axis and having a channel extending therethrough to a distal opening, the bone cement injector at least partially percutaneously insertable into a bone;

a bone cement delivery container removably coupled to a proximal end of the bone cement injector and in fluid communication with the channel;

a distal hydraulic fluid container removably coupled to a proximal end of the bone cement delivery container;

a slave piston having a proximal end disposed and slidably movable in the distal hydraulic fluid container and a distal end disposed and slidably movable in the bone cement delivery container, the distal end of the slave piston and a distal end of the bone cement delivery container defining a first chamber configured to hold a bone cement mixture therein and the proximal end of the slave piston and proximal end of the distal hydraulic fluid container defining a second chamber configured to hold a hydraulic fluid therein, the hydraulic fluid having a lower viscosity than the bone cement mixture;

a hydraulic line operably coupled to the proximal end of the distal hydraulic fluid container via a 3-way stopcock valve selectively acutatable to fluidly communicate the hydraulic line with the second chamber or isolate the hydraulic line from the second chamber;

a proximal hydraulic fluid container removably coupled to and in fluid communication with a proximal end of the hydraulic line, the proximal hydraulic fluid container defining a third chamber configured to hold the hydraulic fluid therein; and an actuator movably coupled to the proximal hydraulic fluid container, the actuator having a master piston and a control mechanism selectively actuatable to move the master piston incrementally within the third chamber or to slidably move the master piston within the third chamber, wherein actuation of the actuator to move the master piston distally in the third chamber causes hydraulic fluid to flow from the third chamber to the second chamber when the stopcock valve is positioned to fluidly communicate the hydraulic line with the second chamber, causing the slave piston to move distally to eject bone cement from the first chamber, through the bone cement injector and into the bone, and wherein delivery of bone cement out of the bone cement injector is ceased substantially instantaneously via one or both of actuation of the stopcock valve to fluidly communicate the second chamber with a bypass chamber such that hydraulic fluid from the second chamber flows to the bypass chamber to cause the slave piston to move proximally and actuation of the actuator to slidably move the master piston proximally, thereby drawing hydraulic fluid from the second chamber into the third chamber to cause the slave piston to move proximally.

2. The system of claim 1, wherein the actuator comprises a shaft having a surface with a plurality of teeth along a length of the shaft, the teeth configured to engage a threaded bore in a proximal portion of the proximal hydraulic fluid container, wherein the teeth are movable by the control mechanism between a first position where they engage the threaded bore to allow incremental movement of the master piston in the third chamber and a second position where they do not engage the threaded bore to allow non-incremental free sliding movement of the master piston in the third chamber.

3. The system of claim 2, wherein in the first position the master piston 1s incrementally moved in the third chamber upon rotation of the control mechanism, and wherein in the second position the master piston is freely slid within the third chamber upon translation of the control mechanism.

4. The system of claim 1, wherein the control mechanism comprises a ratchet and a pawl.

5. The system of claim 4, wherein in the first position the pawl engages the ratchet to permit incremental changes in pressure upon translation of the control mechanism, and wherein in the second position the pawl disengages the ratchet to permit greater than the incremental changes in pressure upon translation of the control mechanism.

6. The system of claim 4, wherein in the first position the pawl engages the ratchet to permit only incremental increases in pressure in the second chamber.

7. A system for delivering bone cement into a bone, comprising:

a bone cement injector extending along a longitudinal axis and having a channel extending therethrough to a distal opening, the bone cement injector at least partially percutaneously insertable into a bone;

a bone cement delivery container removably coupled to a proximal end of the bone cement injector and in fluid communication with the channel;

a master-slave hydraulic assembly removably coupled to a proximal end of the bone cement delivery container, a slave portion of the master-slave hydraulic assembly comprising a slave piston having a distal end disposed and slidably movable in the bone cement delivery container and defining a first chamber configured to hold a bone cement mixture therein between the distal end of the slave piston and a distal end of the bone cement delivery container;

a control mechanism operably coupled to a master portion of the master-slave hydraulic assembly via a 3-way stopcock valve, the control mechanism actuatable to incrementally increase hydraulic pressure to cause the slave piston to move so as to controllably expel the bone cement mixture from the first chamber, through the injector and into bone, the control mechanism further selectively actuatable to increase or decrease hydraulic pressure non-incrementally, wherein delivery of bone cement out of the bone cement injector is ceased substantially instantaneously via one or both of actuation of the stopcock valve to cause a decrease of pressure in the hydraulic assembly and cause the slave piston to move proximally and actuation of the control mechanism to decrease pressure in the hydraulic assembly in a non-incremental manner to cause the slave piston to move proximally.

8. The system of claim 7, wherein the control mechanism comprises a ratchet and a pawl.

9. The system of claim 8, wherein in a first position the pawl engages the ratchet to permit incremental changes in pressure upon translation of the control mechanism, and wherein in a second position the pawl disengages the ratchet to permit greater than the incremental changes in pressure upon translation of the control mechanism.

10. The system of claim 8, wherein in a first position the pawl engages the ratchet to permit only incremental increases in pressure in the second chamber.

* * * * *

UNITED STATES PATENT AND TRADEMARK OFFICE
CERTIFICATE OF CORRECTION

PATENT NO. : 10,568,675 B2
APPLICATION NO. : 15/313080
DATED : February 25, 2020
INVENTOR(S) : Balbierz et al.

It is certified that error appears in the above-identified patent and that said Letters Patent is hereby corrected as shown below:

In the Claims

Column 29, Line 28 reads, ". . . master piston 1s . . ." which should read, ". . . master piston is . . ."

Signed and Sealed this
Fourteenth Day of April, 2020

Andrei Iancu
*Director of the United States Patent and Trademark Office*